（12） United States Patent
Nishibayashi et al.

(10) Patent No.: US 7,387,122 B2
(45) Date of Patent: Jun. 17, 2008

(54) POWDER INHALATOR

(75) Inventors: Toru Nishibayashi, Tokushima (JP);
Shintaro Adachi, Tokushima (JP);
Tetsuya Sato, Tokushima (JP)

(73) Assignees: Otsuka Pharmaceutical Co., Ltd. (JP);
Otsuka Techno Corporation (JP)

( * ) Notice: Subject to any disclaimer, the term of this patent is extended or adjusted under 35 U.S.C. 154(b) by 65 days.

(21) Appl. No.: 10/500,141

(22) PCT Filed: Oct. 8, 2003

(86) PCT No.: PCT/JP03/12866

§ 371 (c)(1),
(2), (4) Date: Jul. 8, 2004

(87) PCT Pub. No.: WO2004/033010

PCT Pub. Date: Apr. 22, 2004

(65) Prior Publication Data

US 2005/0103336 A1    May 19, 2005

(30) Foreign Application Priority Data

Oct. 11, 2002    (JP)    ............................. 2002-298726
May 9, 2003    (JP)    ............................. 2003-132034

(51) Int. Cl.
*A61M 15/00*    (2006.01)
*A61M 15/08*    (2006.01)

(52) U.S. Cl. ........................... 128/203.15; 128/203.19; 128/203.23

(58) Field of Classification Search ........... 128/203.12, 128/203.15, 203.19, 203.22, 203.23, 205.23
See application file for complete search history.

(56) References Cited

U.S. PATENT DOCUMENTS

| 4,046,146 A | 9/1977 | Rosskamp et al. ........... 128/266 |
| 5,437,270 A | 8/1995 | Braithwaite ............ 128/203.15 |
| 5,575,280 A * | 11/1996 | Gupte et al. ........... 128/203.15 |

(Continued)

FOREIGN PATENT DOCUMENTS

EP    0 518 087 A1    12/1992

(Continued)

OTHER PUBLICATIONS

Supplementary partial European Search Report mailed Jul. 26, 2006, 5 pages.

*Primary Examiner*—Justine R. Yu
*Assistant Examiner*—Shumaya Ali
(74) *Attorney, Agent, or Firm*—Finnegan, Henderson, Farabow, Garrett & Dunner, LLP

(57) ABSTRACT

A powder inhalator comprising: a housing; a supply member for holding a powdered drug for a large number of doses and having a drug discharge aperture at its bottom surface; a drug carrier, to which the powdered drug is supplied from the drug discharge aperture of the supply member, and having on its upper surface a measuring recess that has a volume equivalent to one dose of the drug; and an operation member disposed so as to move freely back and forth, and operate the drug carrier; the drug carrier moving in contact with the bottom surface of the supply member to carry the powdered drug loaded into the measuring recess from the position of the drug discharge aperture to an air inhalation channel, wherein the drug carrier is disposed slidably so that the measuring recess moves in a circular manner by sliding the drug carrier.

16 Claims, 34 Drawing Sheets

U.S. PATENT DOCUMENTS

| | | | |
|---|---|---|---|
| 5,740,792 A * | 4/1998 | Ashley et al. | 128/203.15 |
| 6,182,655 B1 | 2/2001 | Keller et al. | 128/203.15 |
| 6,240,918 B1 | 6/2001 | Ambrosio et al. | 128/203.15 |
| 6,332,461 B1 * | 12/2001 | Hyppola | 128/203.15 |
| 6,446,626 B1 | 9/2002 | Virtanen | 128/200.14 |
| 6,718,972 B2 * | 4/2004 | O'Leary | 128/203.15 |
| 6,729,328 B2 * | 5/2004 | Goldemann | 217/35 |
| 2002/0148469 A1 * | 10/2002 | O'Leary et al. | 128/203.15 |
| 2005/0183723 A1 * | 8/2005 | Pinon et al. | 128/203.15 |

FOREIGN PATENT DOCUMENTS

| | | |
|---|---|---|
| EP | 0 916 356 | 5/1999 |
| EP | 0 979 661 | 2/2000 |
| EP | 0 979 661 A1 | 2/2000 |
| WO | WO 91/19524 | 12/1991 |
| WO | WO 92/00771 | 1/1992 |
| WO | WO 92/17233 | 10/1992 |
| WO | WO 95/31237 | 11/1995 |
| WO | WO 97/00703 | 1/1997 |
| WO | WO 97/25086 | 7/1997 |
| WO | WO 98/41262 | 9/1998 |
| WO | WO 01/41850 A1 | 6/2001 |

* cited by examiner

[Figure 4]
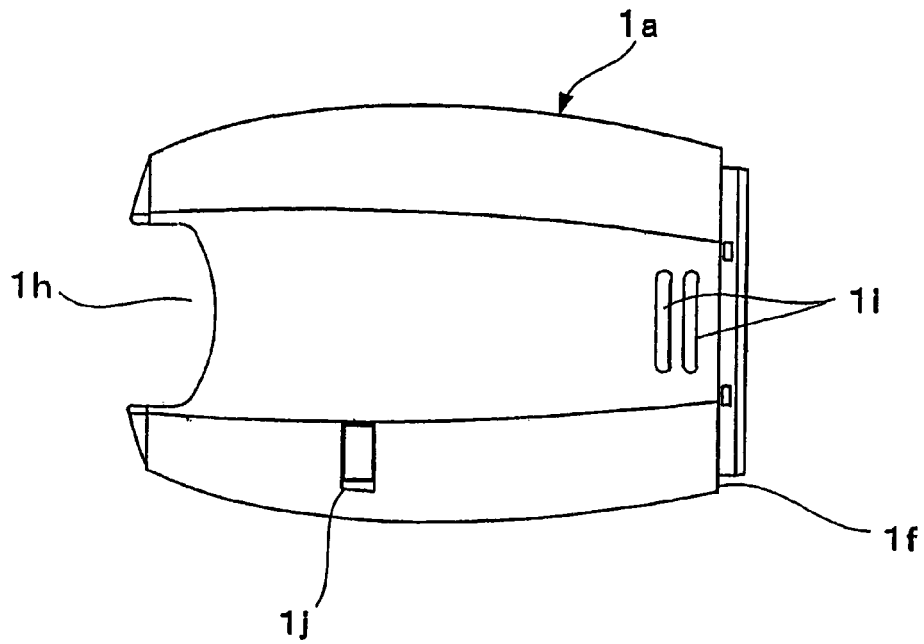
[Figure 5]
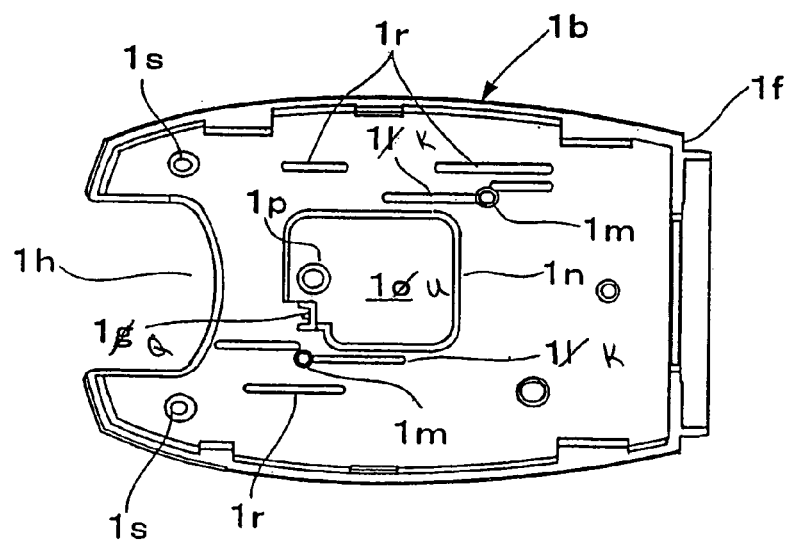
[Figure 6]
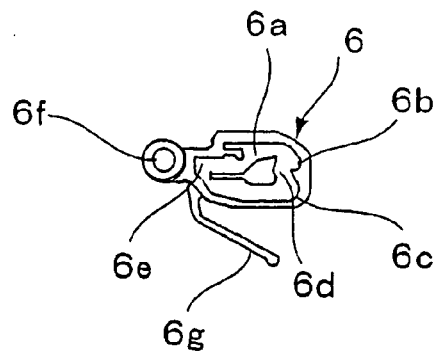

Figure 7
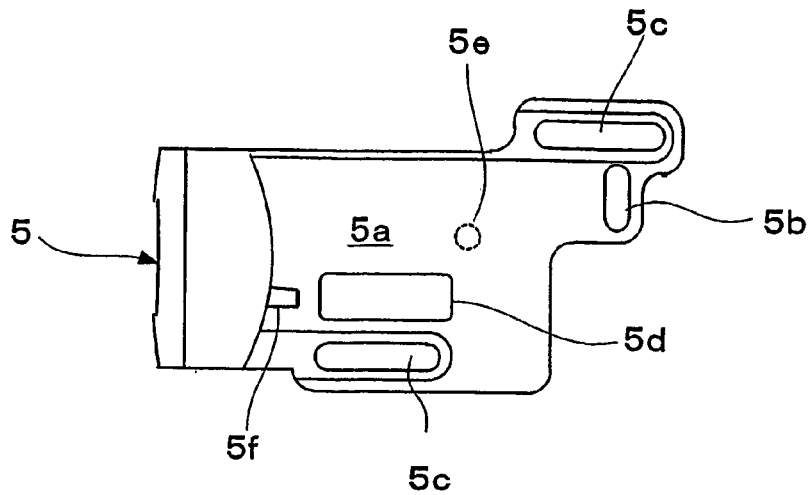
Figure 8
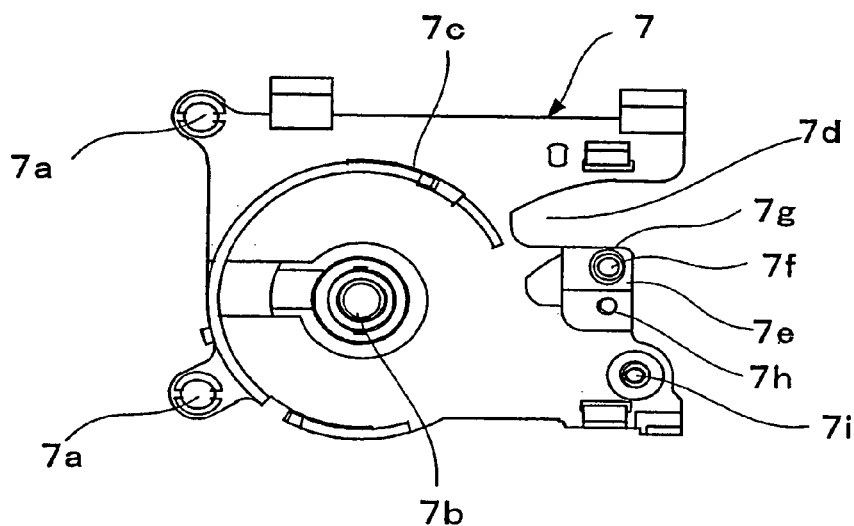
Figure 9
(a)
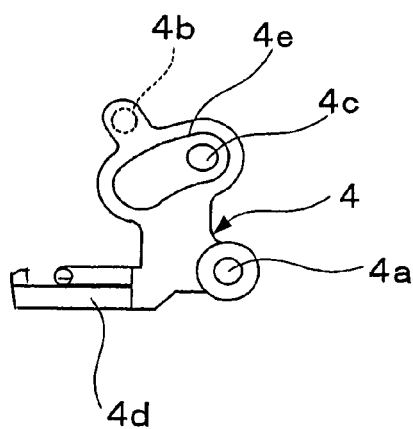
(b)
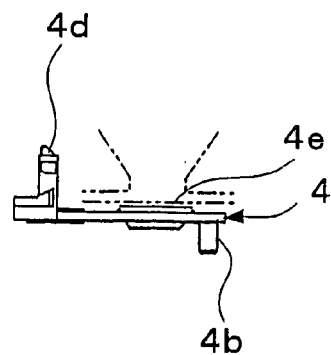

Figure 10
(a)
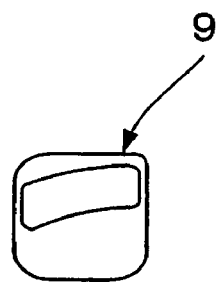
(b)
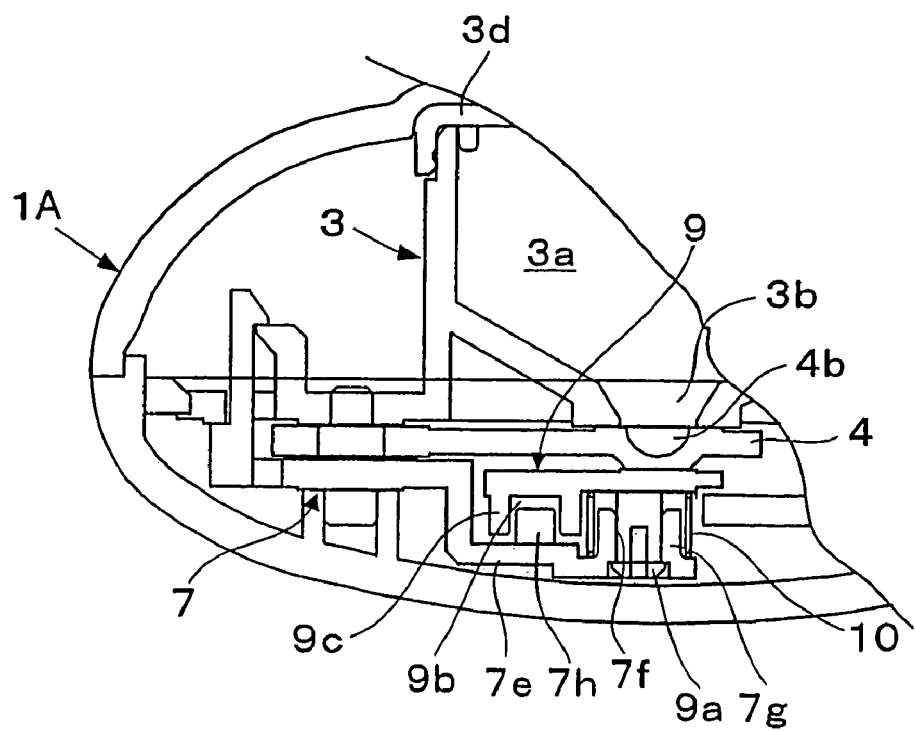

Figure 13
(a)
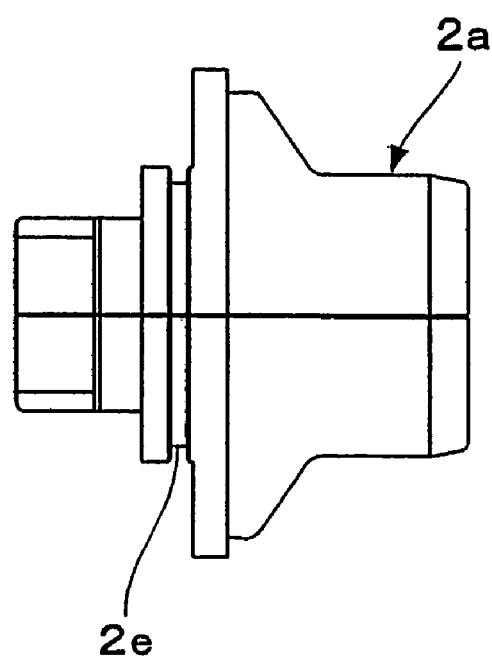
(b)
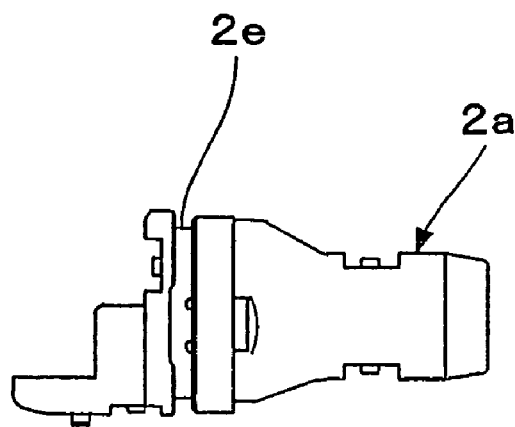

[Figure 27]
(a)
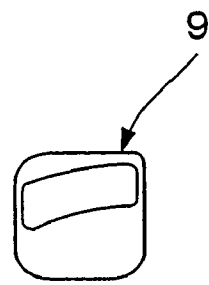
(b)
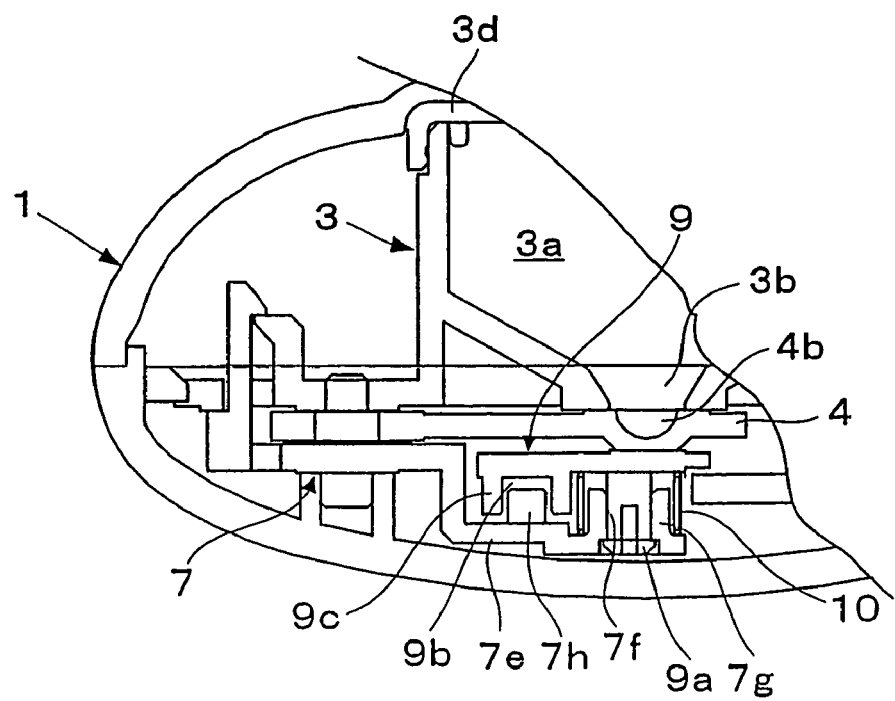

Figure 30
(a)
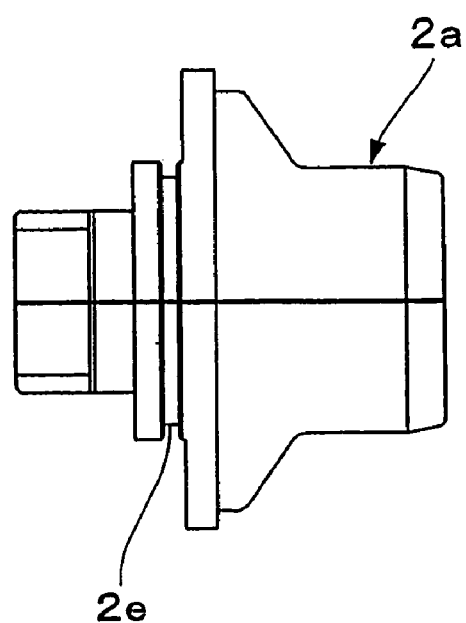
(b)
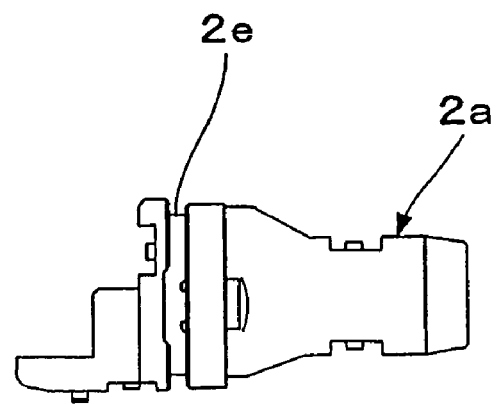

[Figure 31]

Figure 35
(a)
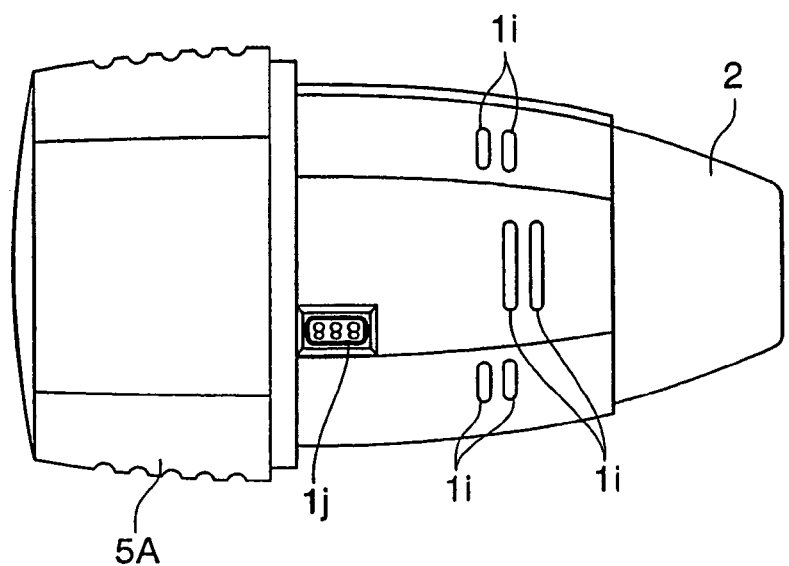
(b)
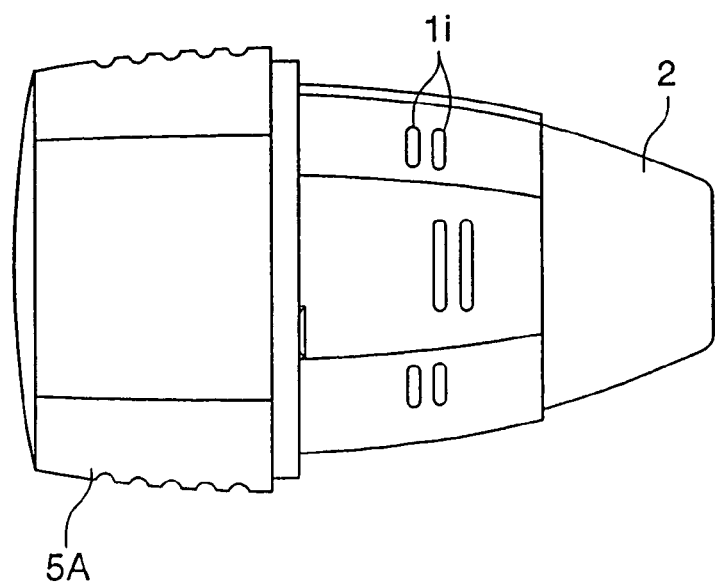

Figure 36
(a)
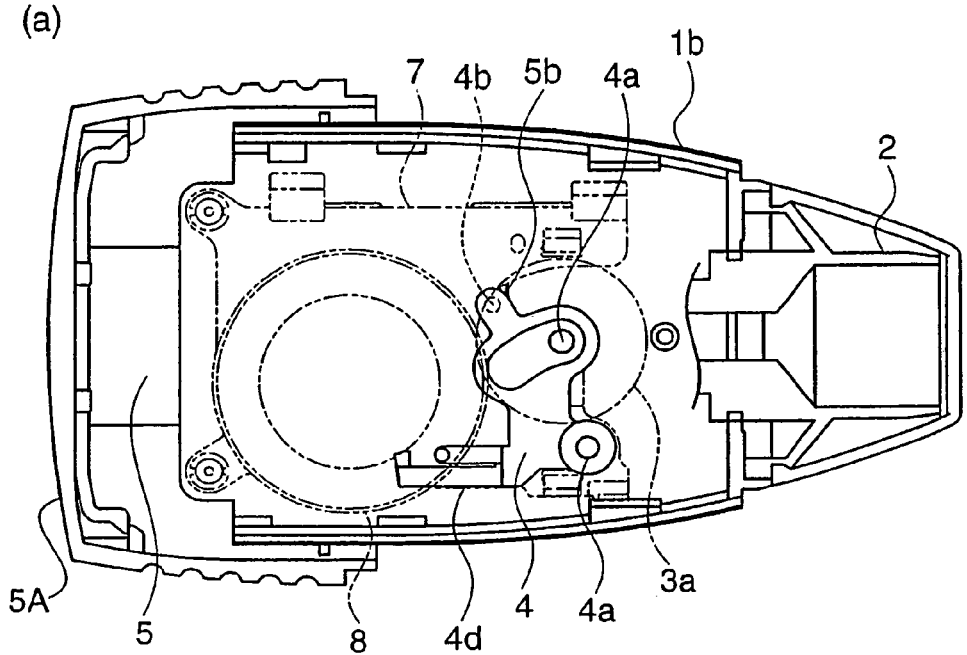
(b)
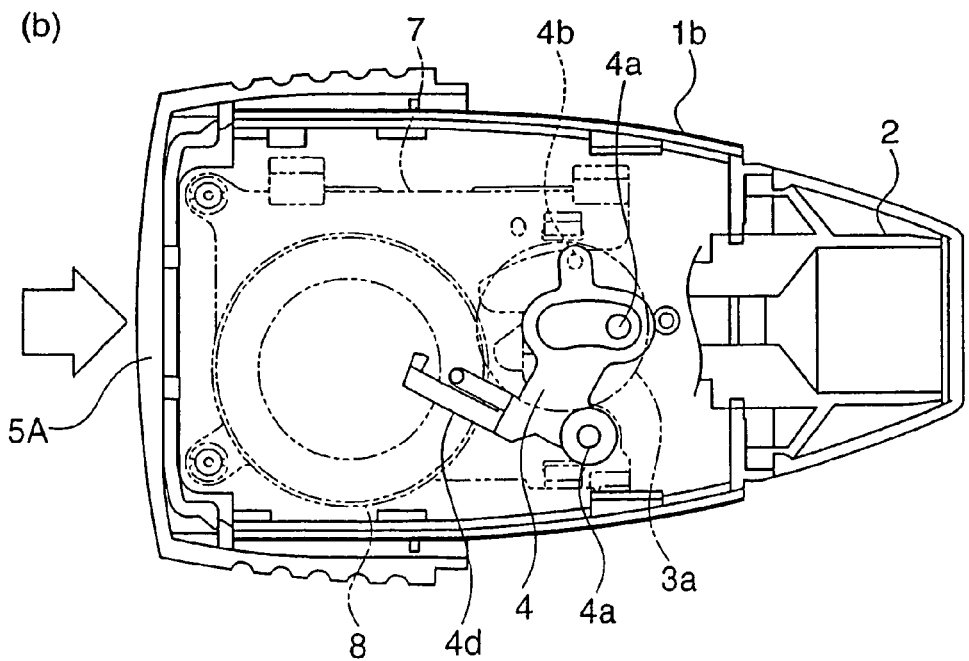

[Figure 38]

Figure 41
(a)
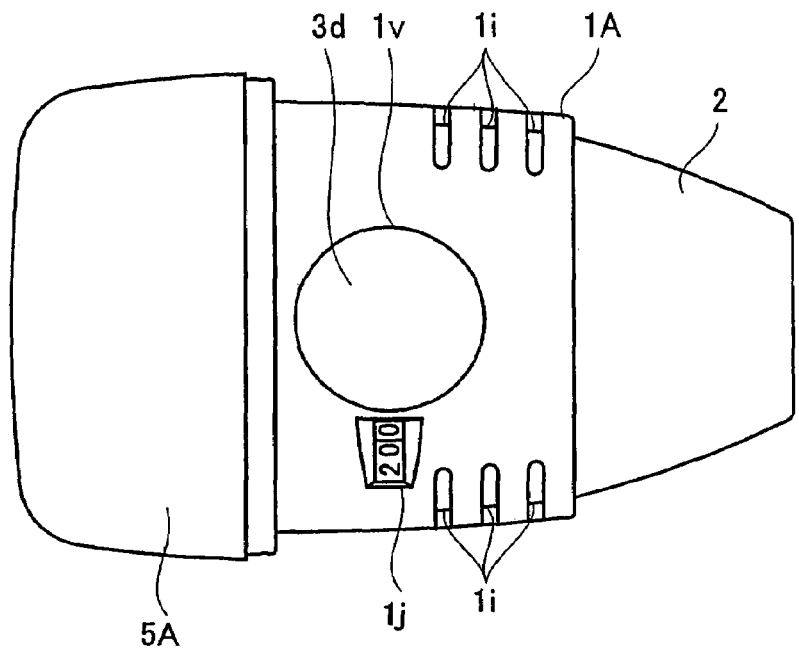
(b)
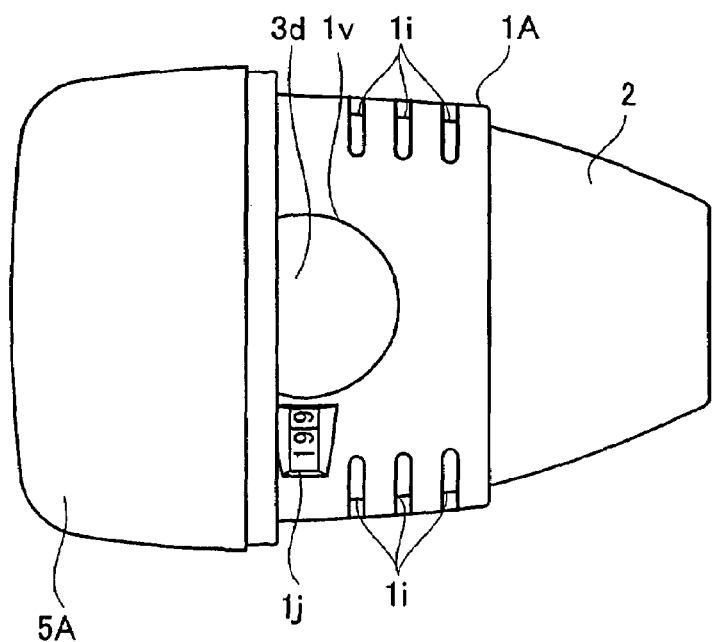

POWDER INHALATOR

TECHNICAL FIELD

The present invention relates to a powder inhalator for supplying powdered pharmaceutical drug for a large number of doses.

BACKGROUND OF THE INVENTION

Powder inhalators of this type are provided with a supply member for containing powdered pharmaceutical drug for a large number of doses, a drug carrier with a measuring recess having a volume equivalent to one dose and an operation member for operating the drug carrier.

To inhale a powdered drug, the drug is loaded into the measuring recess from the drug discharge aperture of the supply member, and the drug carrier is then slid away from the supply member to move the measuring recess in a straight line.

During this movement, the powdered drug loaded into the measuring recess is scraped by one edge of the drug discharge aperture by the sliding action of the drug carrier, and a predetermined quantity of the powdered drug is conveyed into the inhalation channel (Japanese Patent Publication No. 2000-501013).

Such a configuration results in the following two problems.

First, when the powdered drug is scraped, a measuring recess 100 moves in a straight line as shown by the arrow in FIG. 42. As a result, the powdered drug accumulates in the illustrated shaded-area near the edge of a drug discharge aperture 101. As a result, the powdered drug becomes clogged between the supply member of the powdered drug and the drug carrier, which reduces the ability to measure the powdered drug and lowers the operating performance of the drug carrier.

Secondly, static electricity is generated due to friction when the drug carrier slides, and thus the powdered drug adheres to the inside of the powder inhalator. Consequently, the quantitative accuracy and particle containing ratio of the powdered drug is lowered.

The second problem may be solved by shortening the stroke of the measuring recess to reduce the amount of static electricity. However, it is difficult to reduce the amount of static electricity in the above-described conventional powder inhalator due to its configuration, as described below. More specifically, the conventional powder inhalator is configured so that a protecting cap also serves as the operation member and that the measuring recess moves by a distance equivalent to the stroke of the protecting cap in order to expose the mouthpiece. Thus, the measuring recess needs to move the distance that is required to remove the protecting cap from the mouthpiece of the powder inhalator.

Moreover, the operation member is required to move by a certain distance so as to give the user an appropriate feeling of operating the operation member even when a separate operation member is provided for operating the drug carrier. More specifically, the powder inhalator should be configured so as to indicate to the user that the powder inhalator is ready for inhalation through a recognizable operation feeling from the operation member because he/she cannot visually confirm that the measuring recess has moved into an inhalation channel to prepare the powder inhalator for inhalation.

As described above, it is difficult to reduce the amount of friction in a conventional powder inhalator by moving the operation member only a short distance due to its configuration.

The conventional powder inhalator is configured so that the drug carrier is operated by the operation member to convey the powdered drug loaded into the measuring recess toward the mouthpiece (Japanese Published Application No. 5(1993)-237189).

The conventional powder inhalator contains the supply member, the drug carrier, and other members in a housing. The operation member protrudes from the aperture of the housing to the outside to allow the user to manually operate the operation member. Therefore, a gap is created between the operation member and the aperture, and thus, the pharmaceutical drug becomes moistened due to external air flowing from the created gap.

The pharmaceutical drug can be protected against humidity by carrying the powder inhalator in a moisture-proof case, but this creates a need for the user to remove the powder inhalator from the moisture-proof case for every use. Thus, a considerable amount of time is required for the user to inhale the powdered drug. Moreover, portability is lowered by containing the powder inhalator in a moisture-proof case that is necessarily larger than the powder inhalator.

The present invention has been achieved in view of the above-described problems, and provides a powder inhalator which can prevent the powdered drug from becoming clogged between the supply member and the drug carrier, and further can reduce the amount of electrostatic charge without shortening the stroke of the operation member.

In addition thereto, the present invention provides a powder inhalator that has a high moisture-proof effect without employing a separate moist-proof case.

DISCLOSURE OF THE INVENTION

According to one aspect of the present invention, a powder inhalator comprises: a housing; a supply member for holding a powdered drug for a large number of doses and having a drug discharge aperture at its bottom surface; a drug carrier, to which the powdered drug is supplied from the drug discharge aperture of the supply member, and having on its upper surface a measuring recess that has a volume equivalent to one dose of the drug; and an operation member disposed so as to move freely back and forth, and operate the drug carrier. The drug carrier moves in contact with the bottom surface of the supply member to carry the powdered drug loaded into the measuring recess from the position of the drug discharge aperture to an air inhalation channel. In the powder inhalator, the drug carrier is supported pivotably in the housing so that the measuring recess moves in a circular manner by pivoting the drug carrier.

It is preferred that the measuring recess is located at a position between the center of the pivotal movement of the drug carrier and the point at which the operation member engages the drug carrier.

It is preferred that the operation member is a pushbutton and the operation member is pressed to move the measuring recess into the air inhalation channel.

It is preferred that conductivity is imparted to the supply member, the drug carrier and the operation member.

It is preferred that the measuring recess is a spherical concave shape and provided with a bottom.

According to another aspect of the present invention, a powder inhalator comprises: a housing having a mouthpiece in its front portion; a supply member containing powdered drug for a large number of doses; a drug carrier which moves back and forth between the supply member and the mouthpiece to convey a dose of the powdered drug from the supply member toward the mouthpiece; a protecting cap which detachably fits onto the housing from the front side of the housing; and an operation member which operates the drug carrier by moving back and forth, and which is shaped like a cap so as to cover the housing from the rear side of the housing. In the powder inhalator, an opening for operation is provided at the rear side of the housing and a connector is inserted into the opening to connect the operation member to the drug carrier; and the protecting cap joins at the rear end thereof with the front end of the operation member to envelope the housing when covering the housing with the protecting cap.

It is preferred that a baffle is provided so as to prevent air flowing into a gap formed between the housing and the operation member.

It is preferred that a seal member is attached to at least one of the front end of the operation member or the rear end of the protecting cap, and the protecting cap and the operation member are joined to each other via the seal member.

BRIEF DESCRIPTION OF THE DRAWINGS

FIG. 4 is a plan view illustrating the upper-side housing of the powder inhalator.

FIG. 5 is a plan view illustrating the lower-side housing of the powder inhalator.

FIG. 6 is a plan view illustrating a lock member of the powder inhalator.

FIG. 7 is a plan view illustrating an operation member of the powder inhalator.

FIG. 8 is a plan view illustrating a base of the powder inhalator.

FIG. 9(*a*) is a plan view illustrating a drug carrier of the powder inhalator.

FIG. 9(*b*) is a side elevation view illustrating the drug carrier of the powder inhalator.

FIG. 10(*a*) is a plan view of a press member of the powder inhalator.

FIG. 10(*b*) is a cross sectional view illustrating a state where the press member is attached to the base.

FIG. 12(*b*) is a bottom view of the supply member of the powder inhalator.

FIG. 13(*a*) is a plan view illustrating a mouthpiece of the powder inhalator.

FIG. 13(*b*) is a side elevation view of the mouthpiece of the powder inhalator.

FIG. 26(*b*) is a side elevation view illustrating the drug carrier of the powder inhalator.

FIG. 27(*a*) is a plan view of a press member of the powder inhalator.

FIG. 27(*b*) is a cross sectional view illustrating a state where the press member is attached to the base.

FIG. 29(*b*) is a bottom view of the supply member of the powder inhalator.

FIG. 30(*a*) is a plan view illustrating a mouthpiece of the powder inhalator.

FIG. 30(*b*) is a side elevation view of the mouthpiece of the powder inhalator.

FIG. 35(*a*) is a plan view illustrating the powder inhalator before operating.

FIG. 35(*b*) is a plan view illustrating the powder inhalator after operating.

FIG. 36(*a*) is a horizontal cross sectional view illustrating the powder inhalator before operating.

FIG. 36(*b*) is a horizontal cross sectional view illustrating the powder inhalator after operating.

FIG. 41(*a*) is a plan view illustrating the powder inhalator before operating.

FIG. 41(*b*) is a plan view illustrating the powder inhalator after operating.

BEST MODE FOR CARRYING OUT THE PRESENT INVENTION

Hereinafter, the embodiments of the present invention will be described with reference to drawings.

EMBODIMENT 1

Figure 1:
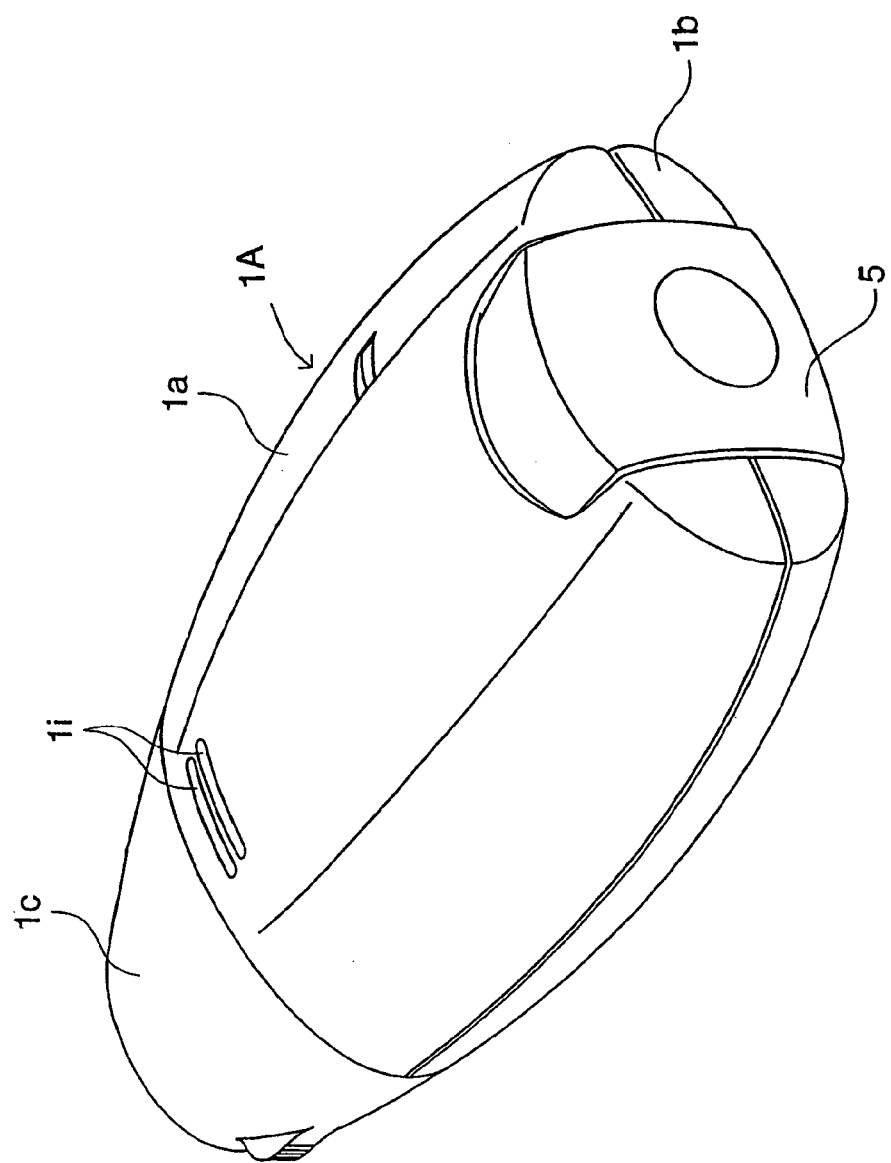
FIG. 1 is a perspective view illustrating a powder inhalator according to Embodiment 1 of the present invention.
Figure 2:
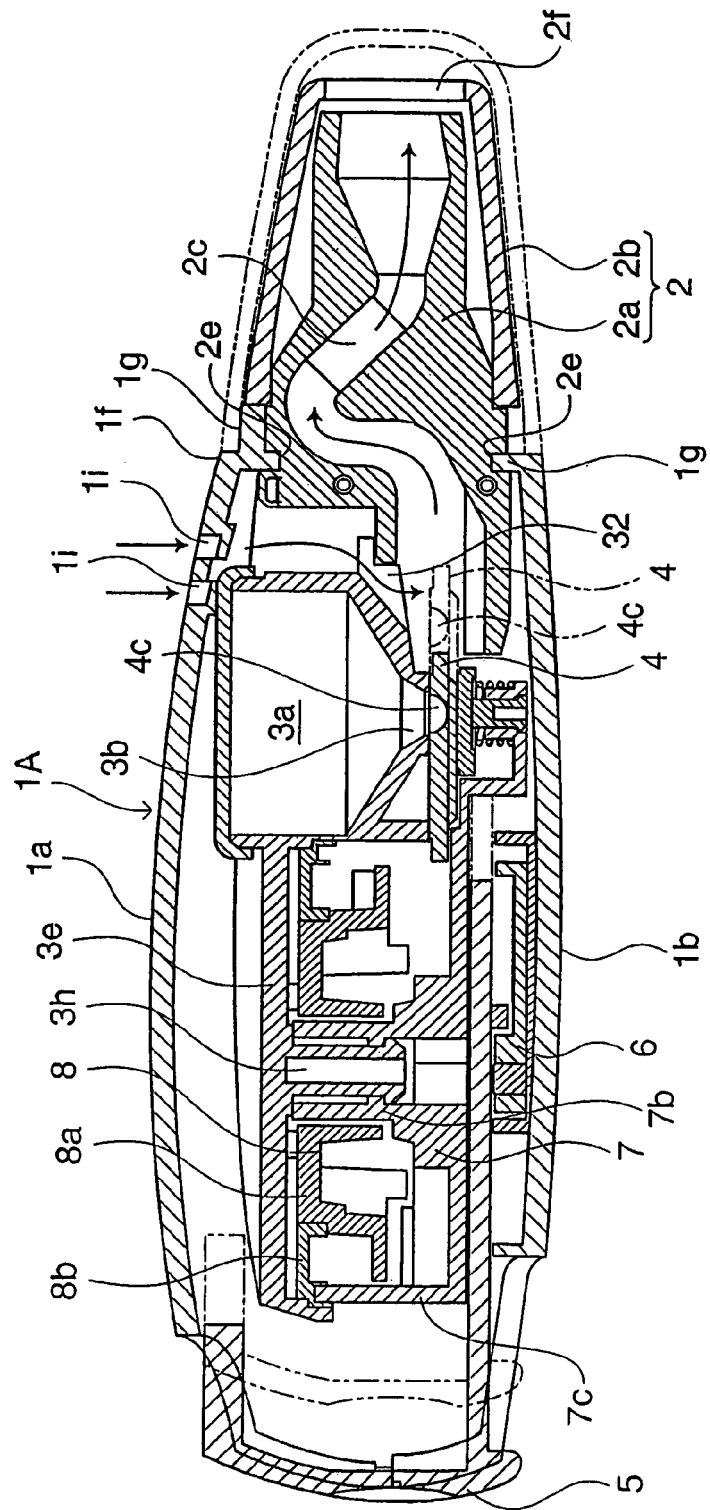
FIG. 2 is an elevational cross sectional view illustrating the powder inhalator.
Figure 3:
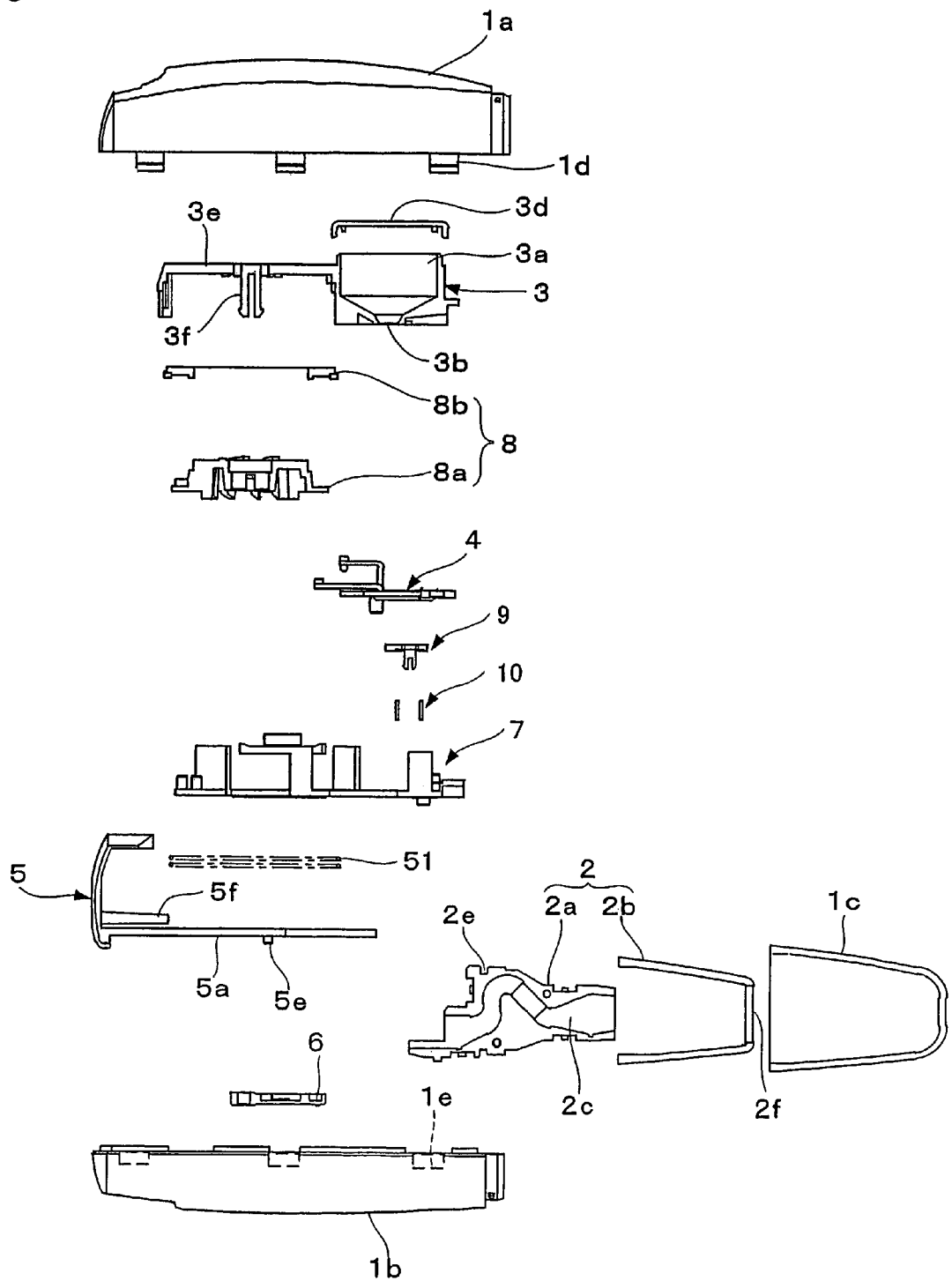
FIG. 3 is a side elevation view illustrating an exploded view of the powder inhalator.
Figure 11:
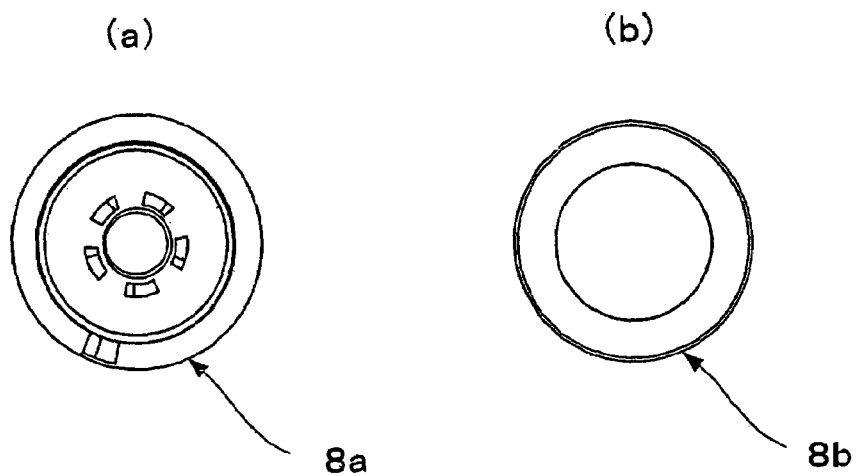
FIG. 11 is a plan view illustrating a counter of the powder inhalator.
Figure 12:
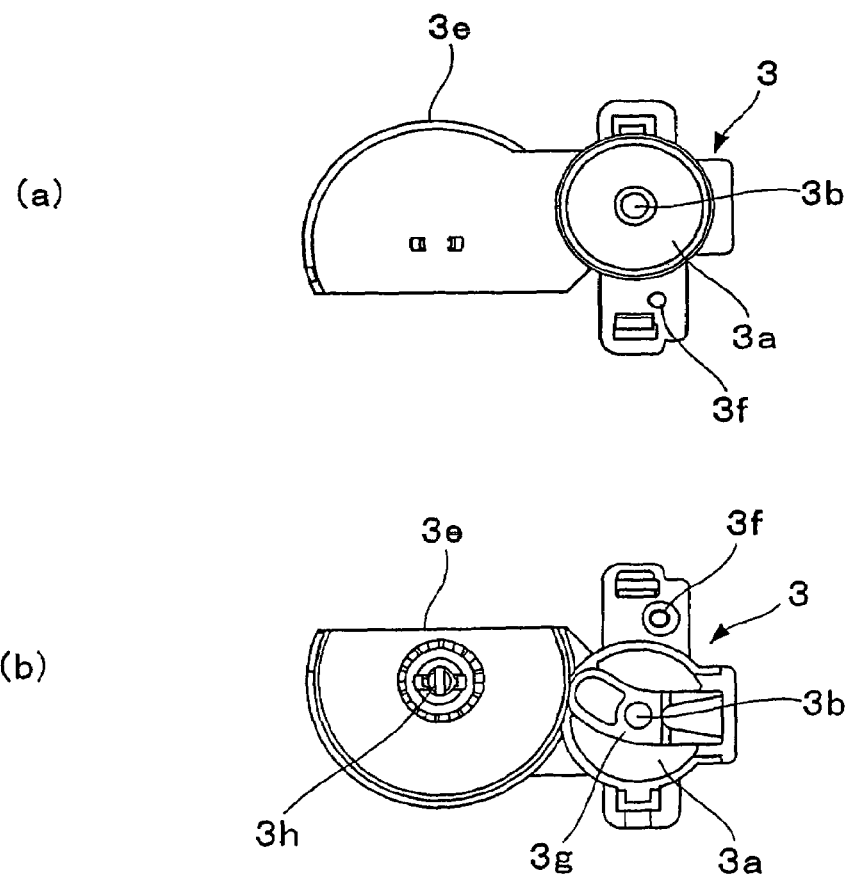
FIG. 12(*a*) is a plan view of a supply member of the powder inhalator.
Figure 14:
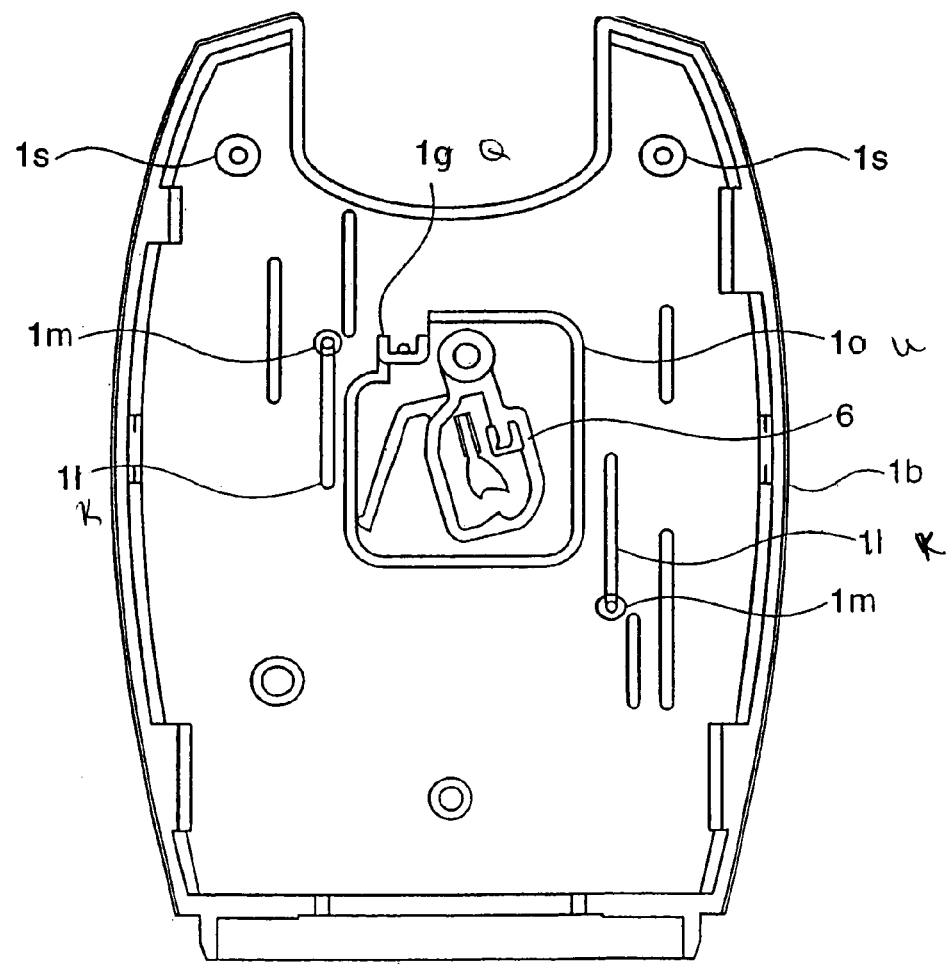
FIG. 14 is a plan view illustrating a stage of assembling the powder inhalator.
Figure 15:
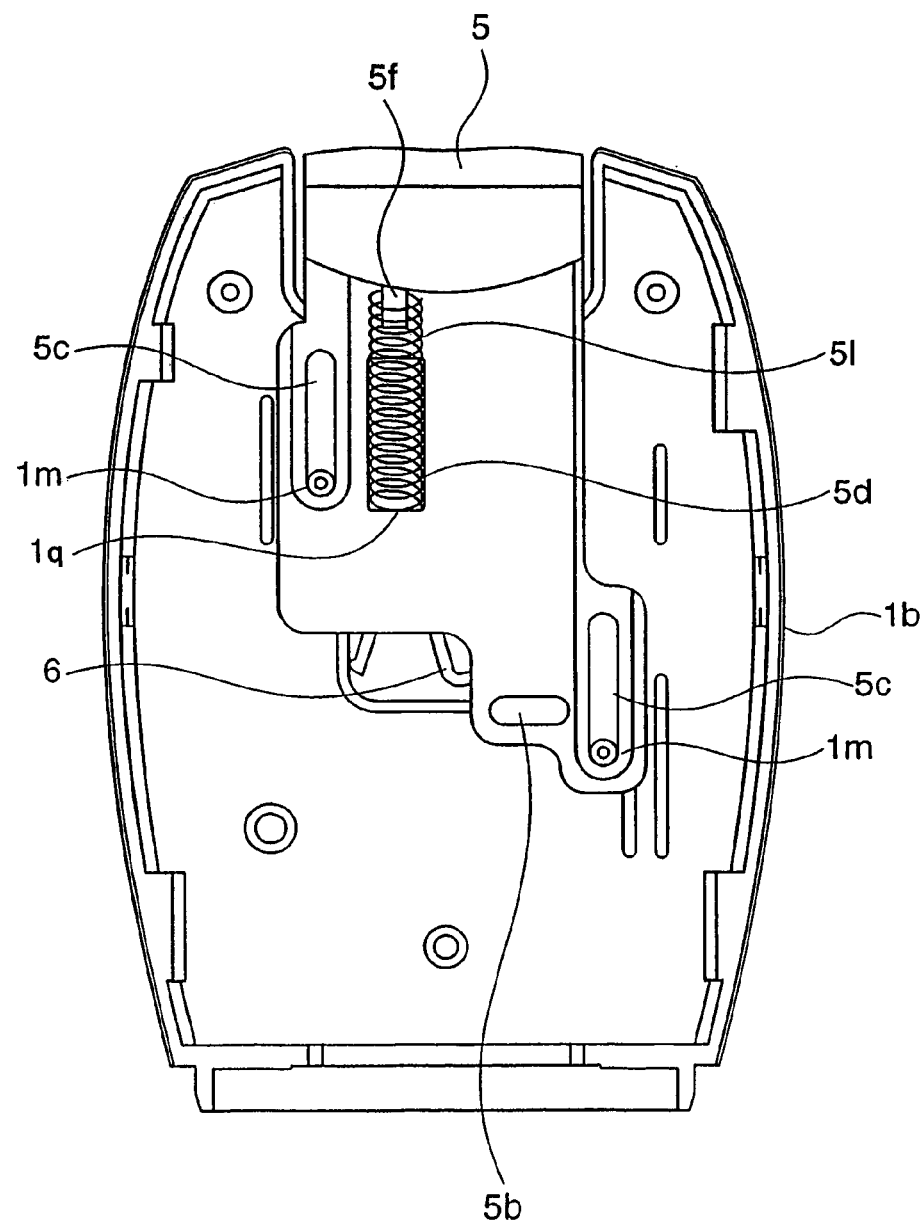
FIG. 15 is a plan view illustrating a stage of assembling the powder inhalator.

FIG. 1 is a perspective view of a powder inhalator. FIG. 2 is a cross sectional view of the powder inhalator. FIG. 3 is a side elevation view of an exploded powder inhalator. As shown in FIGS. 1 through 3, the powder inhalator is provided with a housing 1A, a mouthpiece 2 for active inhalation of powdered drugs, a supply member 3 for containing powdered drug for a large number of doses, a drug carrier 4 for carrying a dose of the powdered drug, an operation member 5 (pushbutton) for operating the drug carrier 4, a lock member 6 for locking the operation member 5, a base 7 and a counter 8 for displaying the number of doses.

The housing 1A is provided with an upper-side housing 1a, a lower-side housing 1b and a protecting cap 1c. The upper-side housing 1a and the lower-side housing 1b are joined to each other by a latch hook 1d and a latch groove 1e shown in FIG. 3 in a snap-in style. The drug carrier 4 can slide as described later, and thus, the housing 1A has a wide breadth so as to ensure a gap for sliding the drug carrier 4.

As shown in FIGS. 2 and 4, an attachment portion 1f for the mouthpiece 2 is provided at each tip portion of the upper-side housing 1a and the lower-side 1b. A pinching projection 1g for pinching the mouthpiece 2 is provided at the attachment portion 1f. A containing portion 1h for the operation member 5 is formed at each end of the upper-side housing 1a and the lower-side housing 1b. An air intake 1i shaped in a long, horizontal slot is provided in the vicinity of the attachment portion 1f for the mouthpiece 2 of the upper-side housing 1a. A window 1j is provided at a location corresponding to the attachment location for a counter 8, through which the counter 8 can be read out.

As shown in FIG. 5, the inside of the lower-side housing 1b is provided with the following members: a linear projection 1k and a guide shaft 1m which guide an operation member 5; a containing unit 1u surrounded by a projection in for containing the lock member 6; a pivot shaft 1p of the lock member 6 provided within the containing unit 1u; a spring-latch projection 1q; a base receiver 1r; and an engagement projection 1s.

The mouthpiece 2 is configured by a body 2a and a cover 2b. A drug inhalation channel 2c for dispersing the powdered drug is formed in the body 2a. An engagement groove 2e is formed at an outer peripheral portion of the body 2a. An air-intake aperture 2f is provided at the cover 2b.

The supply member 3 is provided with a hopper 3a which contains the powdered drugs for about 200 doses. A drug discharge aperture 3b is provided at the bottom end of the hopper 3a. An aperture 3c at the upper-end side of the hopper 3a of the supply member 3 is closed by means of a lid 3d for protecting the powdered drug against humidity. An air-intake grove 32 is formed at the outer wall surface of the hopper 3a. The supply member 3 is further provided with a through hole 3f and a cover 3e having a positioning pin 3h for positioning a counter 8. In addition thereto, a thick-wall part 3g is formed at regions corresponding to the periphery of the drug discharge aperture 3b and a sliding part 4e of the drug carrier 4 so as to reduce an area contacting the surrounding portion of a measuring recess 4c of the drug carrier 4, which will be described later. Thus, the drug carrier 4 contacts only the bottom surface of the thick-wall part 3g.

The operation member 5 is arranged to reciprocate in parallel to the housing 1A and is pressed against elasticity of an operation spring (coil spring) 51. The operation member 5 is provided with a guide plate 5a which is provided with a latching slot 5b and a guiding slot 5c of the drug carrier 4 and an insertion slot 5d through which a spring-latch projection 1q of the lower-side housing 1b is inserted. The bottom surface of the guide plate 5a is further provided with an engagement pin 5e. A spring attachment shaft 5f for attaching an operation spring 51 is provided protruding from the operation member 5.

The lock member 6 is provided with a guide groove 6a, a first switch portion 6b, a second switch portion 6c, an upper engagement portion 6d, a lower engagement portion 6e, an aperture for pivoting 6f and an elastic arm 6g. The lock member 6 is contained in the containing unit 1u of the lower-side housing 1b. The aperture for pivoting 6f receives the pivot shaft 1p formed within the containing unit 1u. The operation member 5 is positioned over the lock member 6 in such a way that the engagement pin 5e of the operation member 5 is inserted into the guide groove 6a of the lock member 6.

Figure 20:
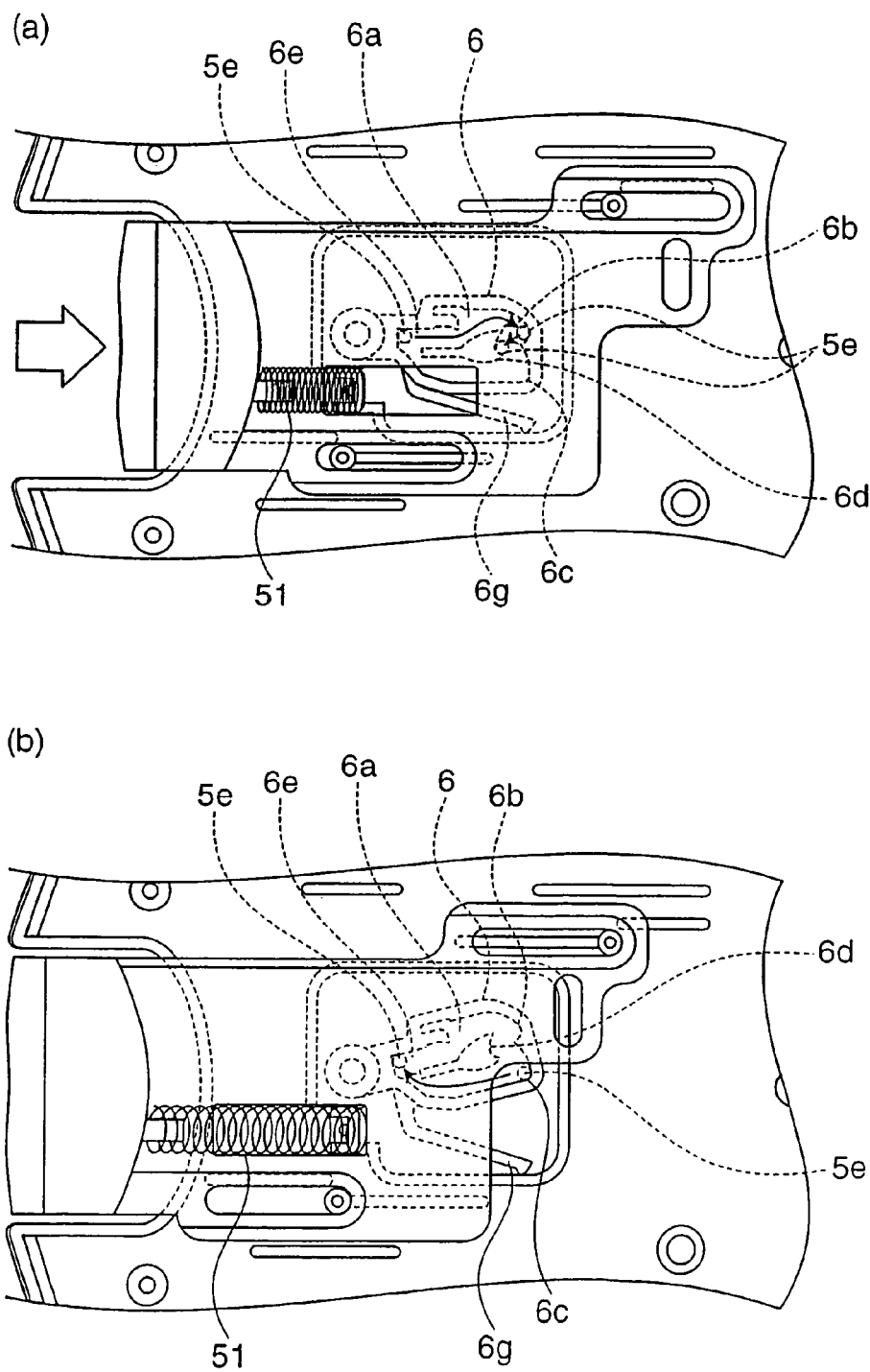
FIG. 20 is a plan view illustrating a lock operation of the operation member of the powder inhalator.

The operation of the lock member 6 will be described. When the operation member 5 is pressed by a finger tip, the engagement pin 5e of the operation member 5 reaches the first switch portion 6b from the lower engagement portion 6e through the guide groove 6a of the lock member 6 (FIG. 20(a)). During this movement, the lock member 6 slides against the elasticity of the elastic arm 6g. Thereafter, the operation member 5 is released, and thus the engagement pin 5e of the operation member 5 engages with the upper engagement portion 6d by means of elasticity of the operation spring 51, whereby the operation member 5 is pressed to be locked. Subsequently, when the operation member 5 is re-pressed, the engagement pin 5e is released from the lower engagement portion 6e by means of elastic restoring force of the elastic arm 6g, to reach the second switch portion 6c (FIG. 20(b)). When pressing force applied to the operation member 5 is released, the engagement pin 5e moves to the lower engagement portion 6e through the guide groove 6a by means of elasticity of the operation spring 51, and thus the operation member 5 returns to the original position (FIG. 20(a)). The whole operation of the powder inhalator will be described later.

The drug carrier 4 is provided with a shaft opening 4a at one end thereof, and a latch pin 4b at the other end thereof as shown in FIG. 9. A single-dose measuring recess 4c having a spherical concave shape and provided with a bottom is formed at a point midway between the shaft opening 4a and the latch pin 4b. The drug carrier 4 is further provided with a ratchet 4d which engages with the counter 8 for rotating the same. The measuring recess 4c may be a through hole.

The upper surface of the drug carrier 4 is partially raised to form an arc-shaped sliding portion 4e as view in a plan, at one end of which the measuring recess 4c is positioned. Thus, the sliding portion 4e alone of the drug carrier 4 contacts the bottom surface of the thick-wall part 3g at the surrounding portion of the drug discharge aperture 3b of the supply member 3 even when the measuring recess 4c moves in a circular manner.

The drug carrier 4 is slidably supported by the pivot pin 7i of the base 7 as described later. The drug carrier 4 engages with the operation member 5 by inserting the latch pin 4*b* of the drug carrier 4 into the latching slot 5*b*.

The sliding portion 4*e* of the drug carrier 4 elastically contacts the bottom surface of the thick-wall part 3*g* at the surrounding portion of the drug discharge aperture 3*b* of the supply member 3 by elastically energizing the drug carrier 4 upwardly by means of a press member 9 which will be described later. Thus, the sliding portion 4*e* of the drug carrier 4 contacts tightly the surrounding portion of the drug discharge aperture 3*b* of the hopper 3*a*, which prevents leakage of the powdered drug from the measuring recess 4*c* of the drug carrier 4.

The base 7 is provided with an engagement aperture 7*a* and a counter support-shaft 7*b*. A counter support-ring 7*c* is provided at the surrounding portion of the counter support-shaft 7*b*. A notch 7*d* is provided in a range in which the engagement pin 4*b* moves due to the sliding action of the drug carrier 4.

The base 7 is provided further with an attachment portion 7*e* for the press member 9. The attachment portion 7*e* is provided with a spring support-shaft 7*g* having an engagement aperture 7*f* and a fix pin 7*h*. The bottom surface of the press member 9 is provided with a boss 9*c* having an engagement projection 9*a* and an engagement aperture 9*b*. As shown in FIG. 10(*b*), the press member 9 is spring-forced upwardly by engaging the engagement aperture 9*b* of the press member 9 with the fix pin 7*h* of the base 7, and engaging the engagement projection 9*a* of the press member 9 with the spring support-shaft 7*g* of the base 7 through which the press spring (coil spring) 10 is inserted. A pivot pin 7*i* is formed in the vicinity of the attachment portion 7*e* of the press member 9.

A counter 8 having a known structure can be employed. More specifically, the counter 8 is provided with a disk having a cam 8*a* representing the ones digit and a wheel with a cam 8*b* representing the tens digit. The disk with cam 8*a* is rotatably supported by the counter support-shaft 7*b* of the base 7, and is fitted into the wheel with cam 8*b*, and is also supported by means of the counter support ring 7*c* of the base 7.

The ratchet 4*d* is activated by the sliding action of the drug carrier 4 and causes the disk with cam 8*a* representing the ones digit to rotate increasing the count. The wheel with cam 8*b* rotates increasing the count at the time of 10th dose. Thus, the dose number can be displayed until the wheel with cam 8*b* attains full count.

It may be configured to leak static electricity by imparting conductivity to material of the supply member 3, the drug carrier 4 and the operation member 5 by adding a conductive filler, such as carbon, thereto.

The members, to which conductivity is imparted, are not limited to the supply member 3, the drug carrier 4 and the operation member 5.

Hereinafter, assembling processes of the powder inhalator will be described.

Initially, the lock member 6 is contained in the containing unit 1*u* of the lower-side housing 1*b* as described above. Thereafter, the operation member 5 is attached to the lower housing 1*b* to be located on the lock member 6. During this process, the guide shaft 1*m* of the lower-side housing 1*b* is inserted into the guiding slot 5*c* of the operation member 5. The spring-latch projection 1*q* of the lower-side housing 1*b* is inserted through the insertion slot 5*d* of the operation member 5. One end of the operation spring 51 inserts through the spring attachment shaft 5*f* of the operation member 5, and the other end thereof is latched at the spring-latch projection 1*q* of the lower-side housing 1*b*.

Figure 16:
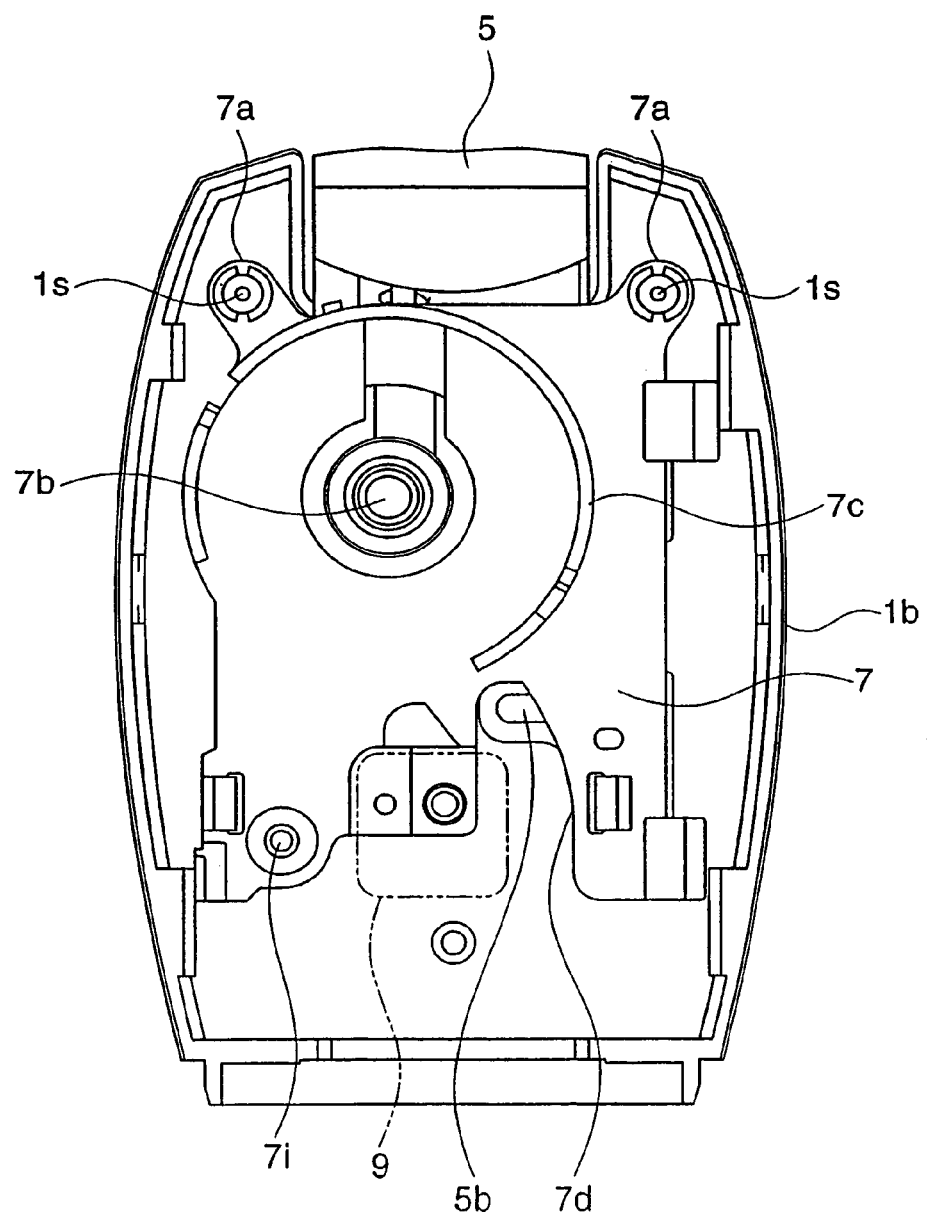
FIG. 16 is a plan view illustrating a stage of assembling the powder inhalator.

Subsequently, the base 7 is mounted on the base receiver 1*r* of the lower-side housing 1*b* and the position of the base 7 is then determined by engaging the engagement aperture 7*a* of the base 7 with the engagement projection is of the lower-side housing 1*b* (FIG. 16).

Figure 17:
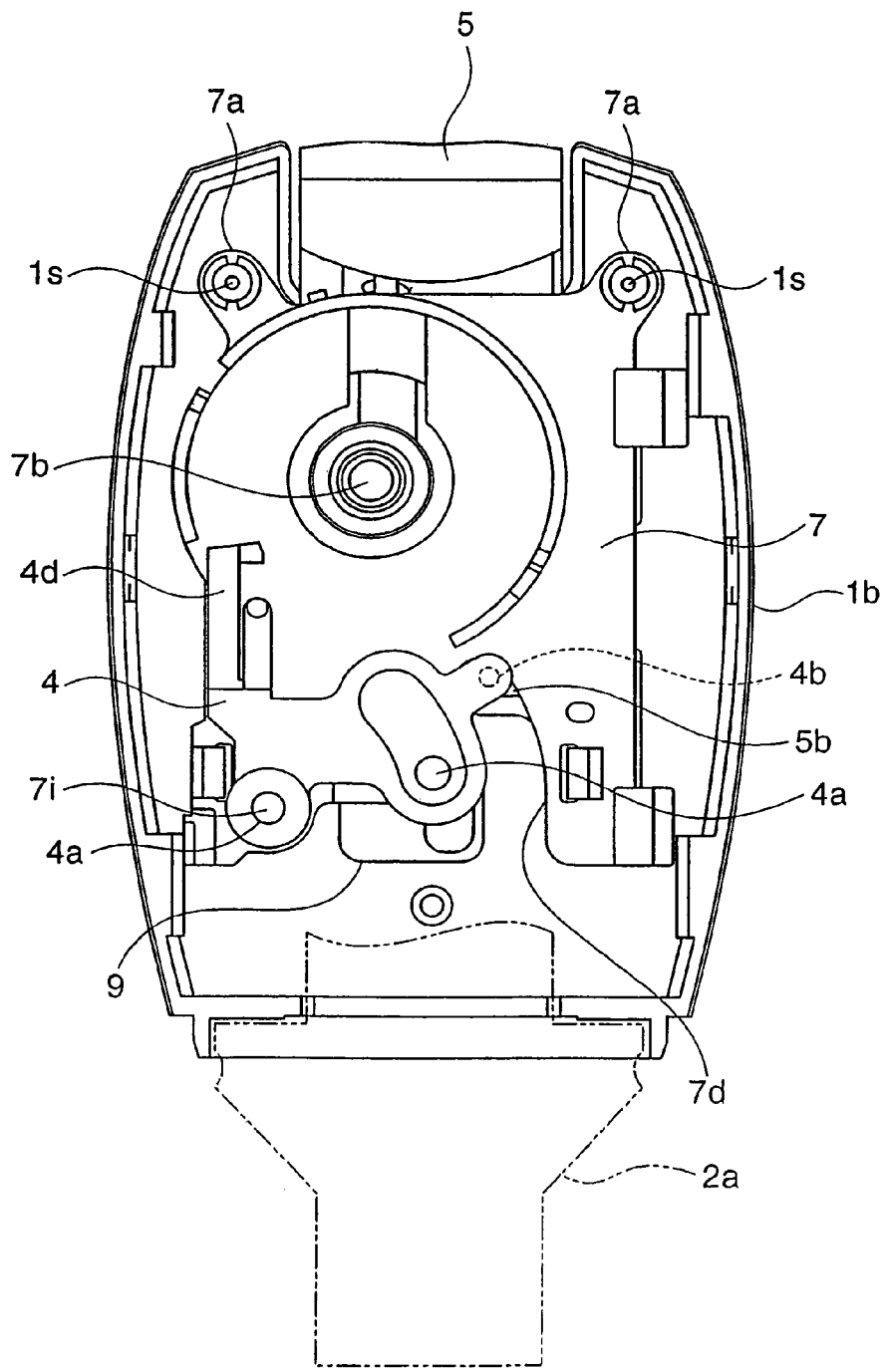
FIG. 17 is a plan view illustrating a stage of assembling the powder inhalator.

The press member 9 is installed on the base 7 as described above, and thereafter the drug carrier 4 is mounted on the base 7 and the press member 9. During this process, the aperture for pivoting 4*a* of the drug carrier 4 and the pivot pin 7*i* of the base 7 are engaged with each other, and the engagement pin 4*b* of the drug carrier 4 then inserts into the latching slot 5*b* of the operation member. 5, whereby the drug carrier 4 engages with the operation member 5 (FIG. 17). The counter 8 is installed on the base 7 as described above. The engagement groove 2*e* of the mouthpiece 2 engages with the pinching projection 1*g* of the lower-side housing 1*b*.

Figure 18:
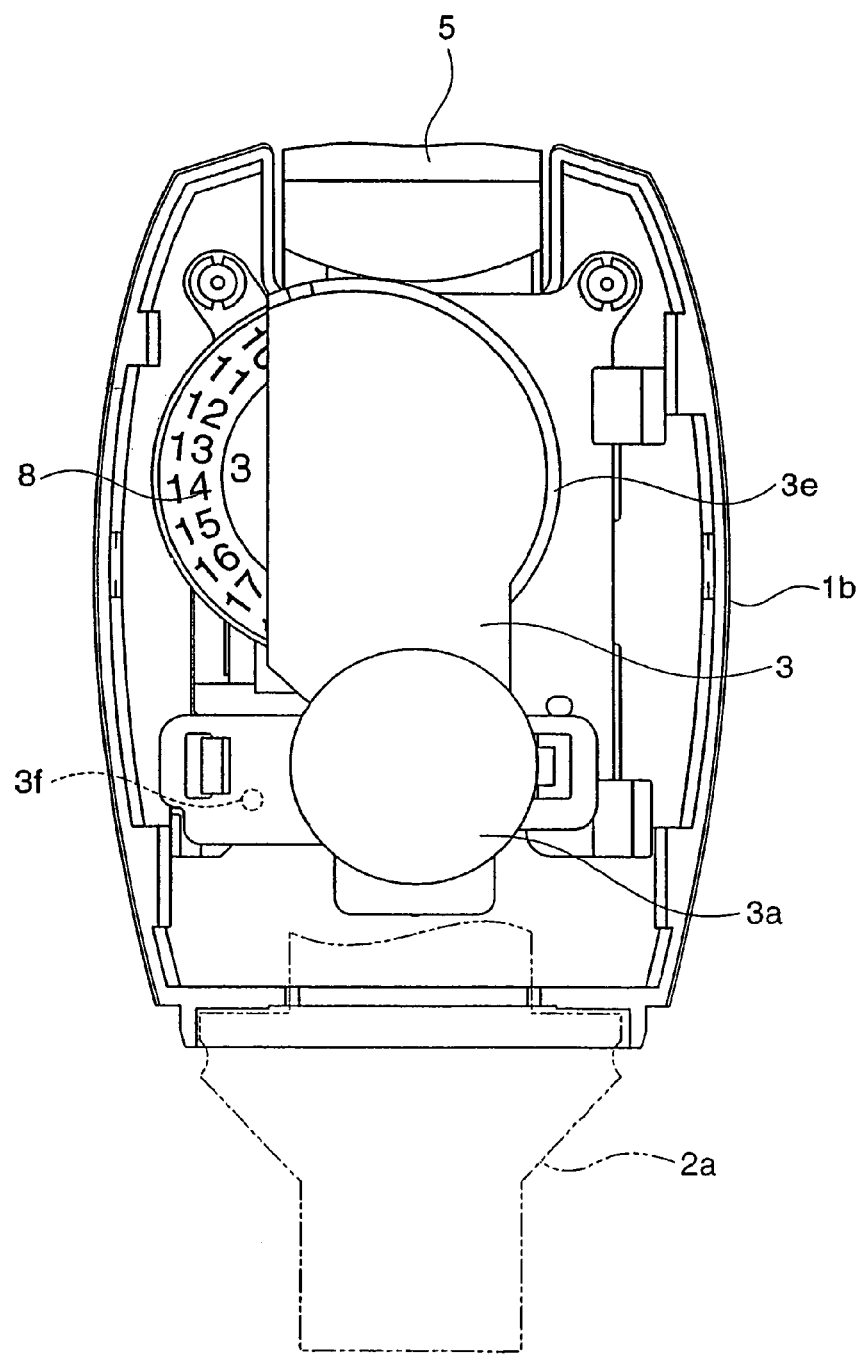
FIG. 18 is a plan view illustrating a stage of assembling the powder inhalator.
Figure 19:
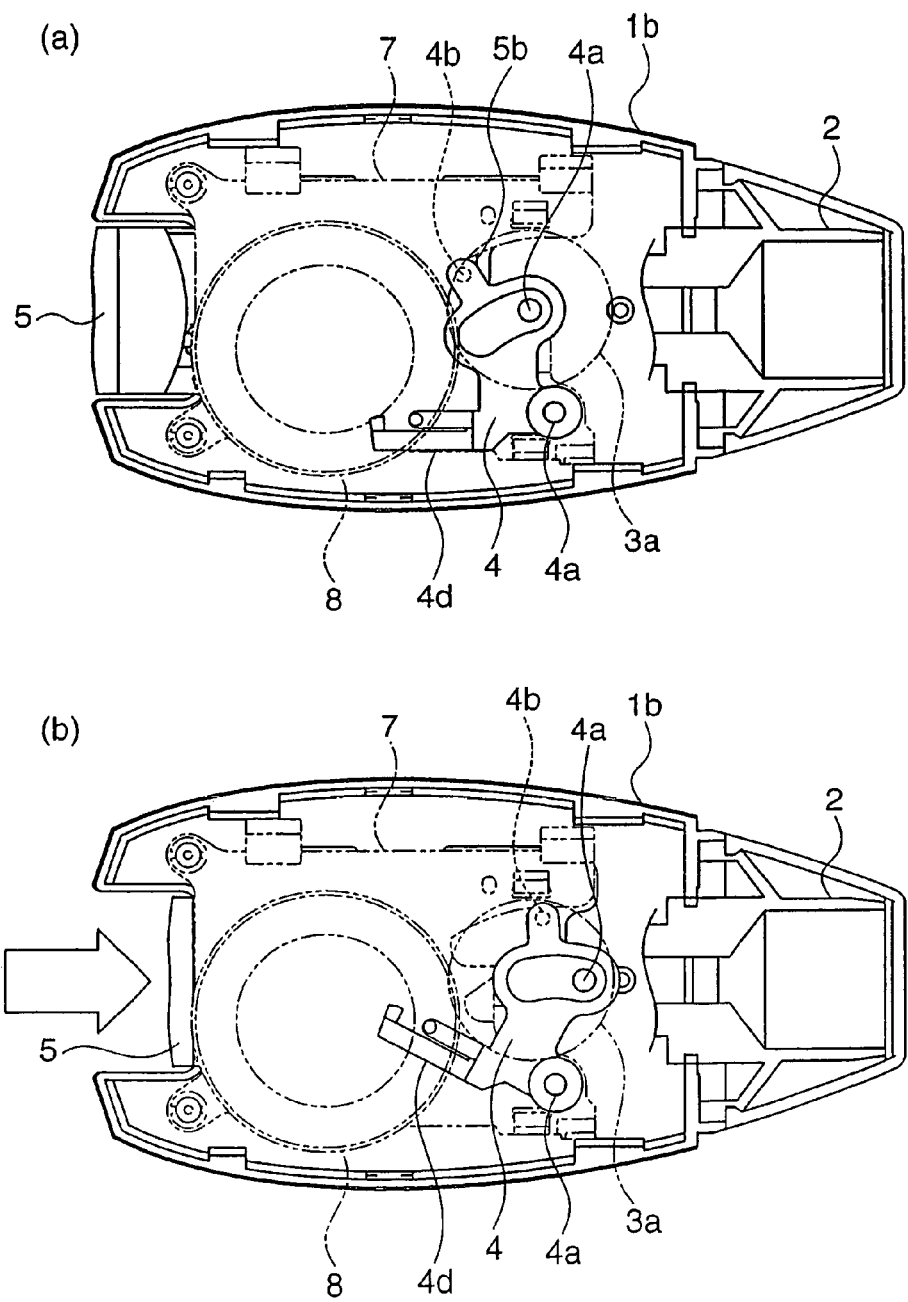
FIG. 19 is a plan view illustrating an operation of the drug carrier of the powder inhalator.

Subsequently, the position of the counter 8 is determined by a cover 3*e* of the supply member 3 by locating the supply member 3 on the drug carrier 4, and inserting the through hole 3*f* of the supply member 3 and the aperture for pivoting 4*a* of the drug carrier 4 through the pivot pin 7*i* of the base 7 in such a way that the drug carrier 4 is slidably supported (FIG. 18).

The position of the supply member 3 is determined by means of the positioning unit formed inside of the upper-side housing 1*a* by joining the upper-side housing 1*a* to the lower-side housing 1*b*. And then, the pinching projection 1*g* of the upper-side housing 1*a* engages with the engagement groove 2*e* of the mouthpiece 2. Finally, the cover 2*b* engages with the body 2*a* of the mouthpiece 2.

As described above, the powder inhalator is assembled by stacking members from the bottom up. Therefore, the assembling processes are clarified and thus the productivity is improved. Moreover, screws are not required, which further increases the productivity.

The powder inhalator configured thus can improve measurability of the powdered drug by means of the measuring recess 4*c* when operated as follows.

As shown in FIG. 2, before the operation member 5 is pressed, the drug carrier 4 is positioned at a drug loading position where the measuring recess 4*c* of the drug carrier 4 is aligned with the drug discharge aperture 3*b* of the supply member 3.

When the operation member 5 is pressed to be locked, the drug carrier 4 slides and thus the measuring recess 4*c* moves into a gap in the vicinity of an air-intake groove 32 of the hopper 3*a* from the drug loading position as represented by a chain double-dashed line in FIG. 2. During this movement, the powdered drug loaded within the measuring recess 4*c* is scraped by the thick-wall part 3*g* at the surrounding portion of the drug discharge aperture 3*b*. Thus, one dose of the powdered drug is carried to a gap in the vicinity of the air-intake groove 32.

Subsequently, the inside of the housing 1A is rendered to be a negative pressure by means of air-intake pressure of a patient when the patient inhales air into the housing 1A from the air-intake aperture 2*f* of the mouthpiece 2. Thus, external air is inhaled into the housing 1A from the air intake 1*i* of the housing 1A to reach the drug inhalation channel 2*c* of the mouthpiece 2 through the air-intake groove 32 of the mouthpiece 2 shown by an arrow in FIG. 2. Thus, air impact is applied to the powdered drug loaded in the measuring recess 4*c* of the drug carrier 4, and the powdered drug is then dispersed within the drug inhalation channel 2*c* of the mouthpiece 2. Hence, the powdered drug reaches the inside of lungs with the inhaled air through the air-intake aperture 2f.

The operation member 5 is returned to the original position, and thus the drug carrier 4 swings back to return to the drug loading position under the drug discharge 3b of the supply member 3.

As described above, when the supply member 5 is pressed or returned, the sliding portion 4e of the drug carrier 4 slides with respect to the surrounding portion of the drug discharge aperture 3b of the supply member 3, and the measuring recess 4c of the drug carrier 4 reciprocates in a circular manner between a position corresponding to the drug discharge aperture 3b and a position in the gap in the vicinity of the air-intake groove 32.

The measuring recess 4c of the drug carrier 4 is positioned at a midpoint between the shaft opening 4a of the drug carrier 4 (center of the pivotal movement of the drug carrier) and the latch pin 4b of the drug carrier 4 (the point at which the operation member engages the drug carrier). Thus, stroke of the measuring recess 4c is shorter than that of the operation member 5. Therefore, the slide distance of the measuring recess 4c (surrounding portion) is shortened, which can minimize static electricity amount and can improve measurability of the powdered drug by means of the measuring recess 4c, as compared to the conventional powder inhalator in which the measuring recess moves by the same distance as the operation member 5.

Figure 21:
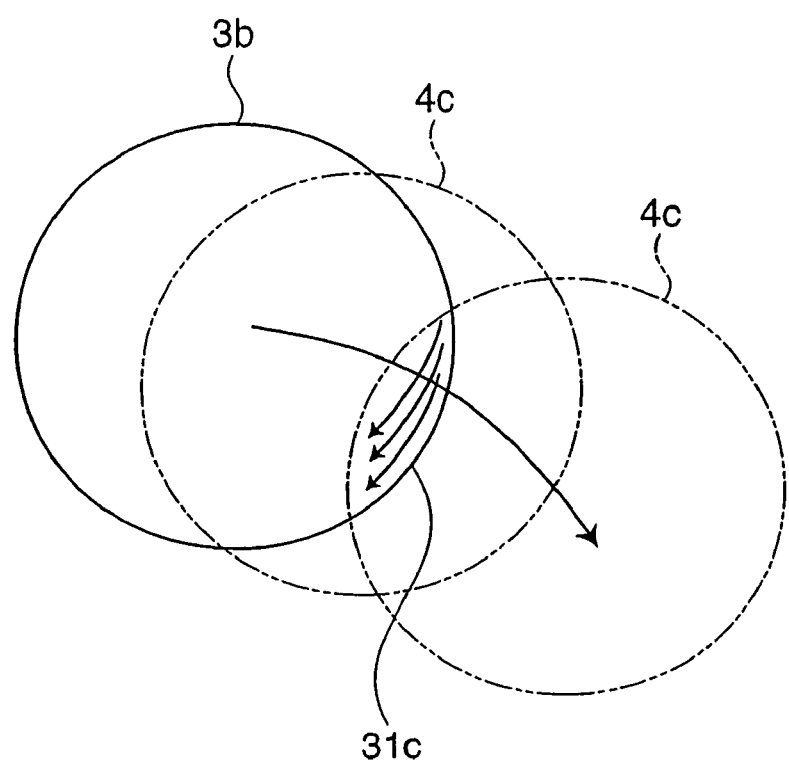
FIG. 21 is a view schematically illustrating a scraping operation of the powdered drug by the powder inhalator.

The measuring recess 4c reciprocate in a circular manner as shown in FIG. 21. Thus, the powdered drug flows along an aperture wall 31c of the drug discharge aperture 3b of the hopper 3a as shown by the arrow in FIG. 21 when the powdered drug is scraped. Consequently, the powdered drug accumulates at the vicinity of the aperture wall 31c of the drug discharge 3b, which can prevent the powdered drug from entering a gap between the supply member 3 and the drug carrier 4.

The powder inhalator is disposed when the powdered drug is completely exhausted.

EMBODIMENT 2

Figure 22:
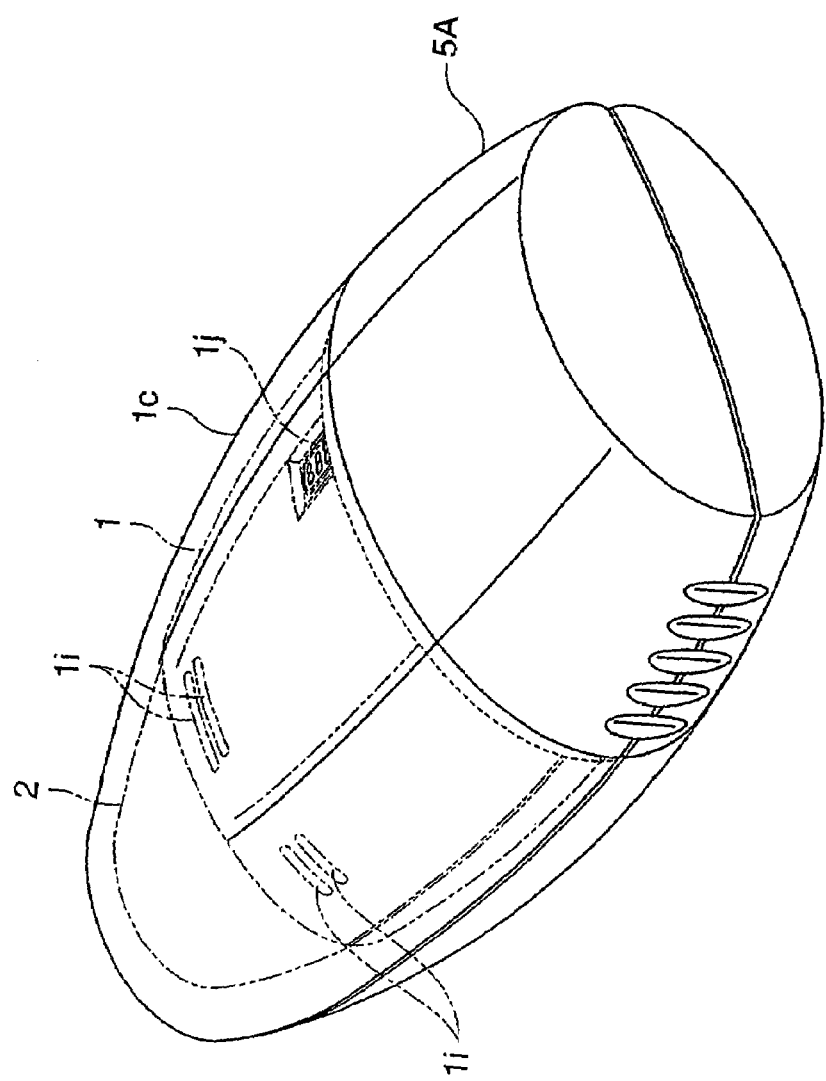
FIG. 22 is a perspective view illustrating a powder inhalator according to Embodiment 2 of the present invention.
Figure 23:
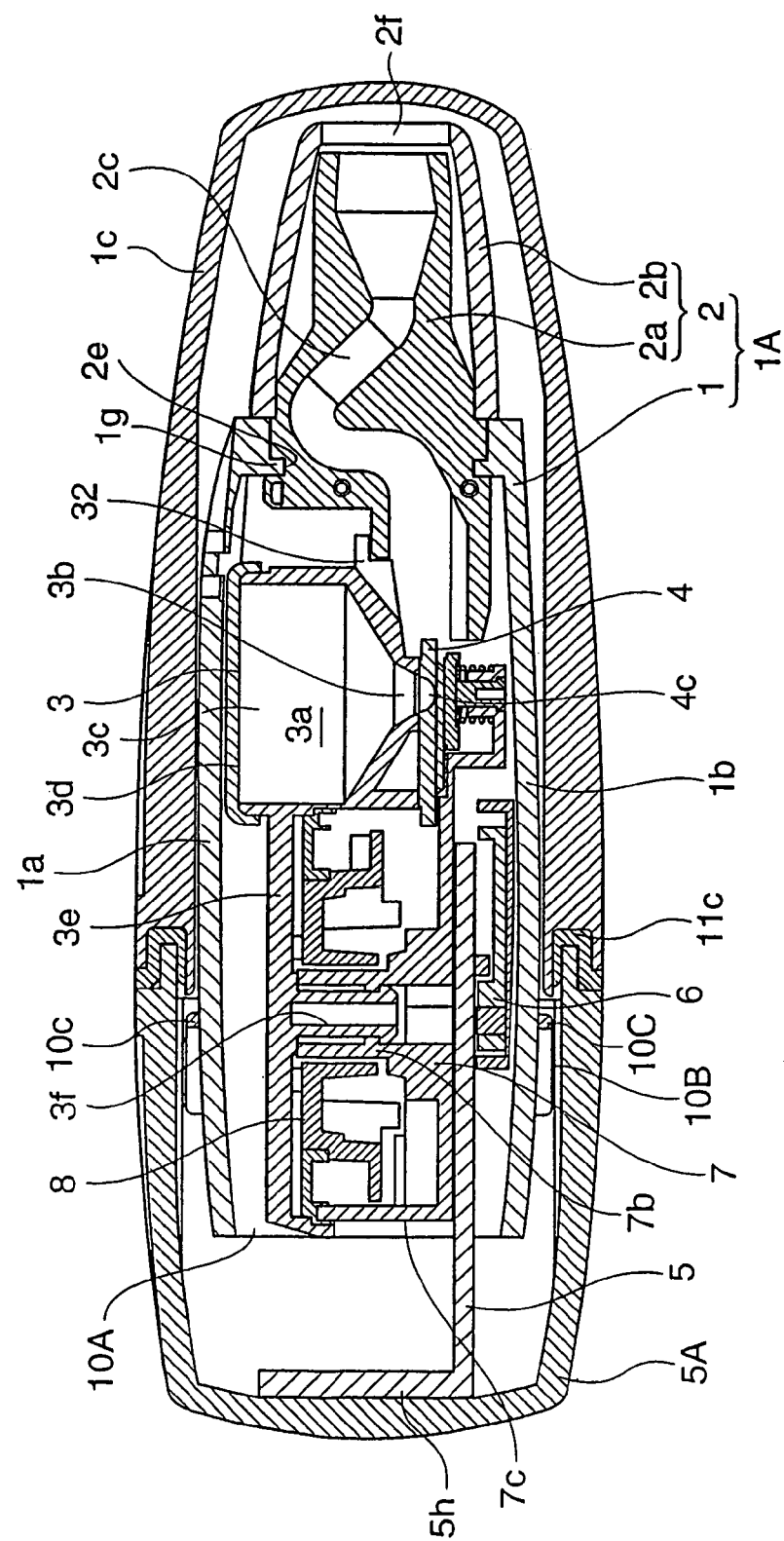
FIG. 23 is an elevational cross sectional view illustrating the powder inhalator.

FIG. 22 is a perspective view of a powder inhalator. FIG. 23 is a cross sectional view of the powder inhalator. The powder inhalator is provided with a housing 1A having a housing body 1 and a mouthpiece 2, a protecting cap 1c, a supply member 3 for containing powdered drug for a large number of doses, a drug carrier 4 for carrying a dose of the powdered drug, an operation member 5A for operating the drug carrier 4, a connector 5 for establishing connection between the drug carrier 4 and the operation member 5A, a lock member 6 for locking the operation member 5A via the connector 5, a base 7 and a counter 8 for displaying the number of doses.

As shown in FIG. 23, the housing body 1 is provided with an upper-side housing 1a and a lower-side housing 1b. At a rear end of the housing body 1 is provided with an aperture 10A for operation through which the connecter 5 is inserted.

The upper-side housing 1a and the lower-side housing 1b are joined to each other by a latch hook and a latch groove (not shown) in a so-called snap-in style. As shown in FIGS. 22 and 35, air intakes 1i shaped in a long, horizontal slot are formed at a center of the front portion and both sides of the upper housing 1a. A window 1j is provided at a portion corresponding to an attachment portion for a counter 8, through which the display of the counter 8 can be read out.

Figure 31:
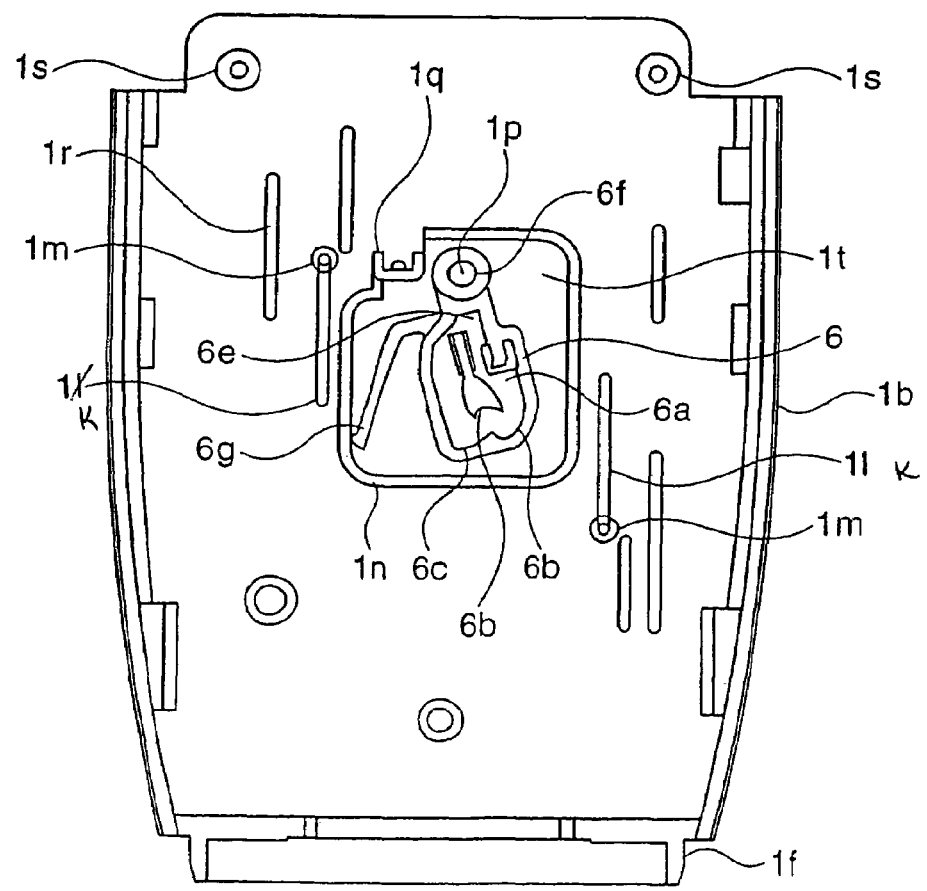
FIG. 31 is a plan view illustrating a stage of assembling the powder inhalator.
Figure 32:
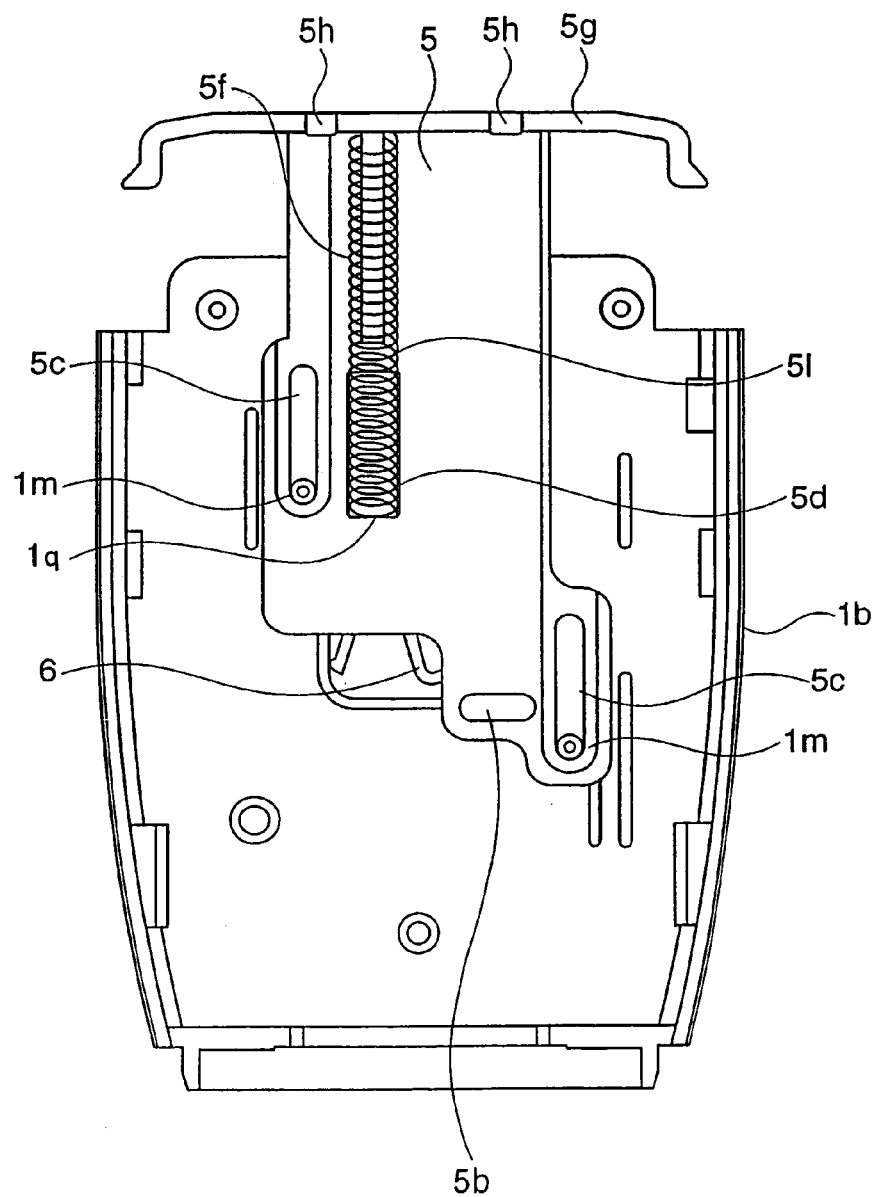
FIG. 32 is a plan view illustrating a stage of assembling the powder inhalator.

As shown in FIG. 31, the inside of the lower-side housing 1b is provided with the following members: a linear projection 1k and a guide shaft 1m which guide the connector 5; a containing unit it surrounded by a projection 1n for containing the lock member 6; a pivot shaft 1p of the lock member 6 provided within the containing unit 1t; a spring-latch projection 1q; a base receiver 1r; and an engagement projection 1s.

The mouthpiece 2 is configured by a body 2a and a cover 2b as shown in FIG. 23. A drug inhalation channel 2c for dispersing the same is formed in the body 2a. An engagement groove 2e is formed at an outer peripheral portion of the body 2a. An air-intake aperture 2f is provided at the cover 2b.

Figure 29:
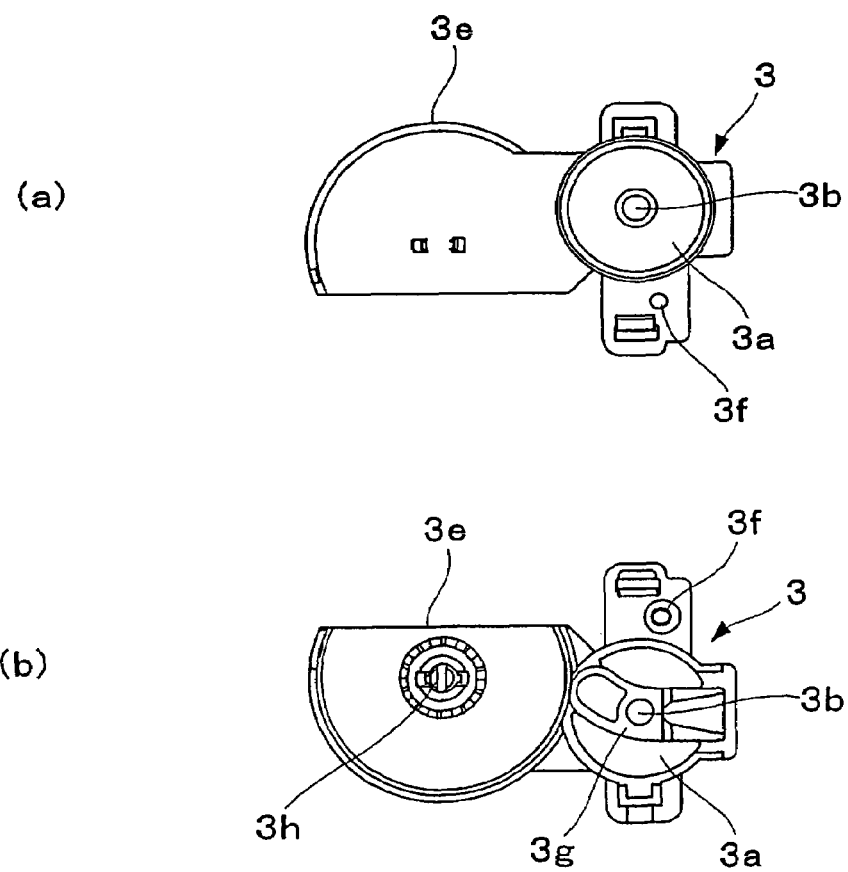
FIG. 29(*a*) is a plan view of a supply member of the powder inhalator.

As shown in FIGS. 23 and 29, the supply member 3 is provided with a hopper 3a which contains the powdered drug for about 200 doses. A drug discharge aperture 3b is provided at the bottom end of the hopper 3a. An aperture 3c at the upper-end side of the hopper 3a of the supply member 3 is closed by means of a lid 3d for protecting the powdered drug against humidity. An air-intake grove 32 is formed at the outer wall surface of the hopper 3a. The supply member 3 is further provided with a through hole 3f and a cover 3e having a positioning pin 3h for positioning a counter 8. In addition thereto, a thick-wall part 3g is formed at regions corresponding to the periphery of the drug discharge aperture 3b and a sliding portion 4e of the drug carrier 4 so as to reduce an area contacting the surrounding portion of a measuring recess 4c of the drug carrier 4, which will be described later. Thus, the drug carrier 4 contacts only the bottom surface of the thick-wall part 3g.

As shown in FIGS. 22 and 23, the protecting cap 1c is set to a size which covers front portions of the mouthpiece 2 and the housing body 1, and has a seal member 11c formed by elastomer or the like at a rear end.

Figure 24:
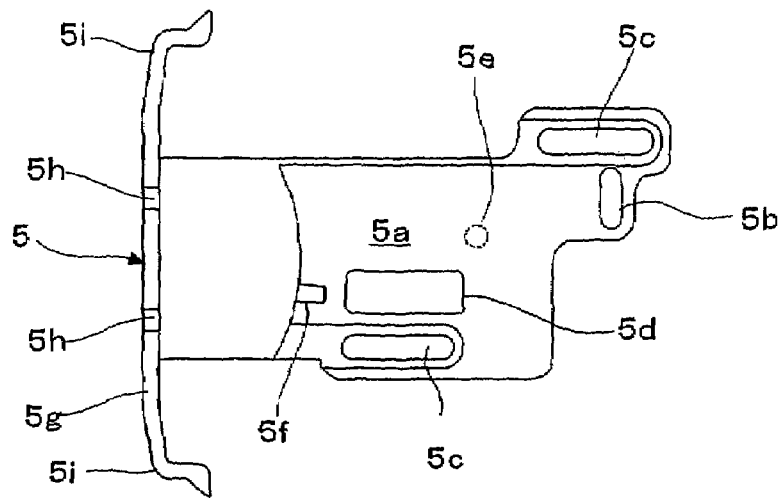
FIG. 24 is a plan view illustrating a connector of the powder inhalator.
Figure 37:
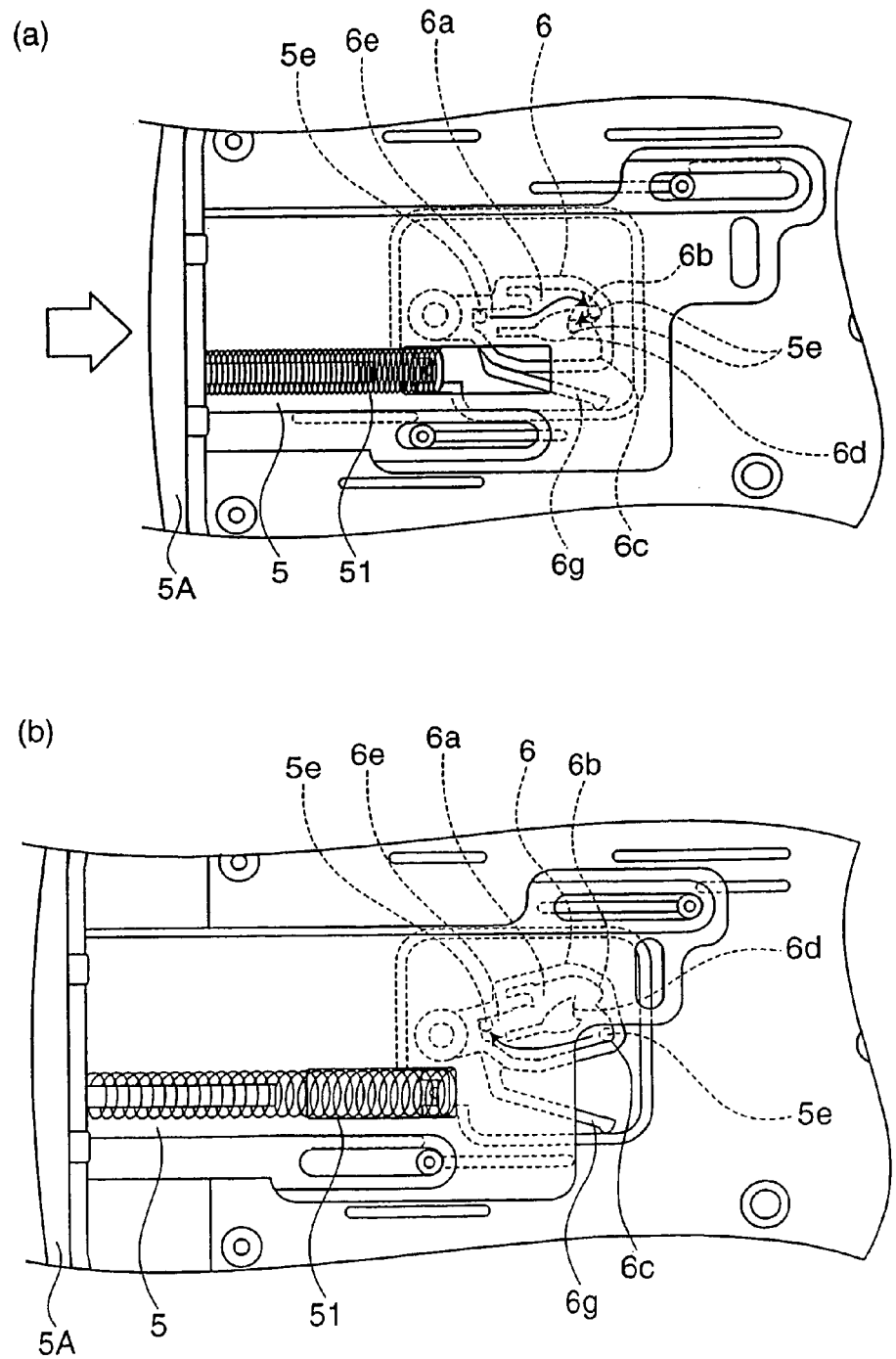
FIG. 37 is a plan view illustrating a lock operation of the operation member of the powder inhalator.

The connector 5 is arranged to reciprocate in parallel to the housing body 1 and is pressed against elasticity of an operation spring (coil spring) 51 as shown in FIG. 37. As shown in FIG. 24, the connector 5 is provided with a guide plate 5a which is provided with a latching slot 5b and a guiding slot 5c of the drug carrier 4 and an insertion slot 5d through which a spring-latch projection 1q of the lower-side housing 1b is inserted. The bottom surface of the guide plate 5a is further provided with an engagement pin 5e. A spring attachment shaft 5f for attaching an operation spring 51 is provided protruding from the operation member 5. At a rear end of the guide plate 5a is formed an L-shaped attachment portion 5g for attaching the operation member 5A. An engagement aperture 5h is formed at the attachment portion 5g. At both sides of the attachment portion 5g is formed a latch elastic portion 5i.

Figure 34:
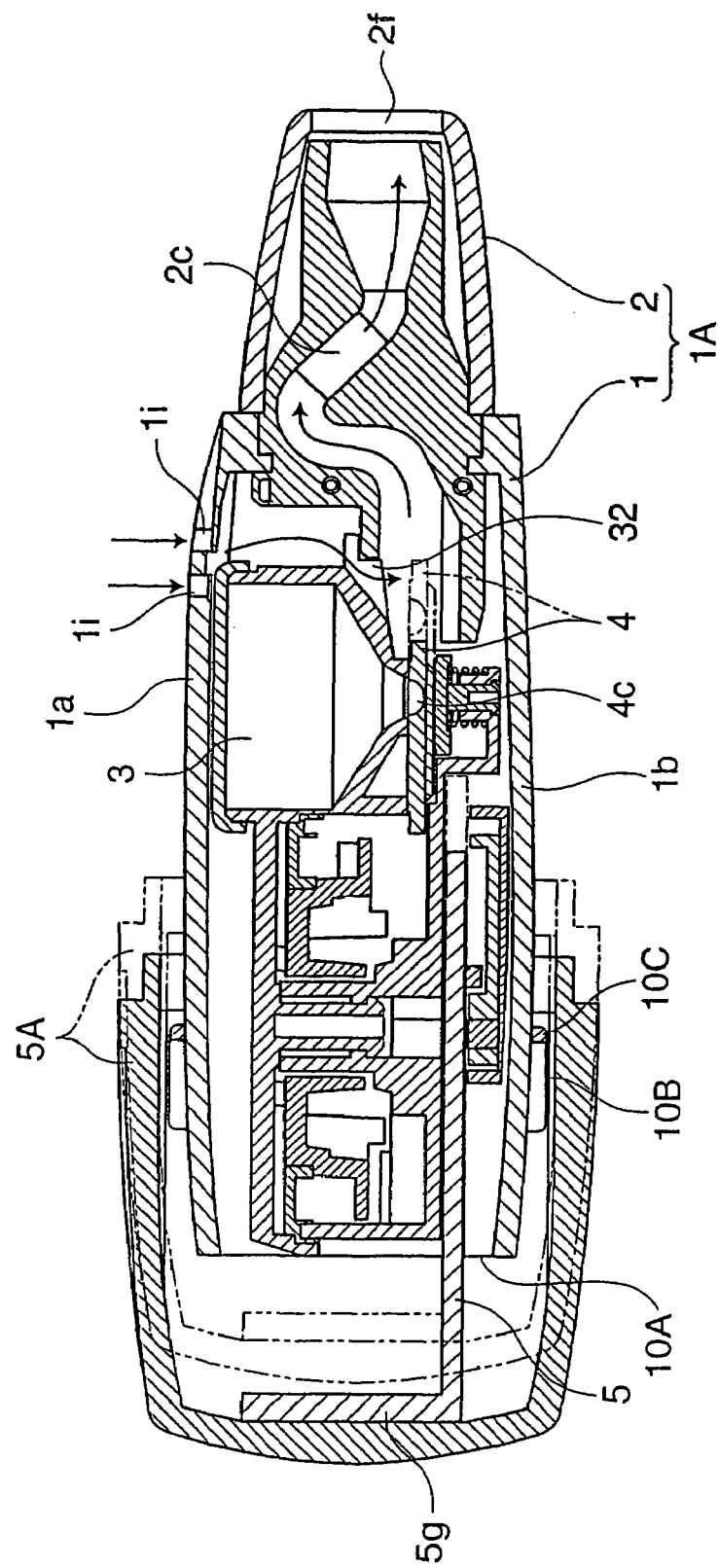
FIG. 34 is an elevational cross sectional view illustrating inhalation operation of the powder inhalator.

The operation member 5A is shaped like a cap, and covers an aperture 10A by covering the rear portion of the housing body 1 and is provided at the rear portion of the housing body in such a way as to move back and forth as shown in FIGS. 22 and 34. A small gap 10B is formed between the operation member 5A and the housing body 1. A baffle 10c is formed at the whole outer peripheral portion of the housing body so that external air cannot flow into the housing body 1 from the gap 10B through the aperture 10A. Because the operation member 5A covers the rear portion of the housing body 1, the external air inflow path that extends from the inlet of the gap 10B to the, powdered drug contained in the housing body 1A is lengthened, making it difficult for external air to enter. At the bottom surface of the operation member 5A are formed an engagement projection 51A and a latch projection 52A. The engagement projection 51A engages with the engagement aperture 5h of the connector 5, and the latch elastic portions 5i of the connector 5 are latched at the latch projection 52A with elastic formation.

The lock member 6 is provided with a guide groove 6a, a first switch portion 6b, a second switch portion 6c, an upper engagement portion 6d, a lower engagement portion 6e, an aperture for pivoting 6f and an elastic arm 6g as shown in FIG. 31. The lock member 6 is contained in the containing unit 1t of the lower-side housing 1b. The aperture for pivoting 6f receives the pivot shaft 1p formed within the containing unit 1u. The connector 5 is positioned on the lock member 6 in such a way that the engagement pin 5e of the connector 5 is inserted into the guide groove 6a of the lock member 6.

The operation of the lock member 6 will be described. When the connector 5 is pressed via the operation member 5A, the engagement pin 5e of the connector 5 reaches the first switch portion 6b from the lower engagement portion 6e of the lock member 6 through the guide groove 6a (FIG. 37(a)). During this movement, the lock member 6 slides against the elasticity of the elastic arm 6g. Thereafter, the operation member 5A is released, and thus the engagement pin 5e of the connector 5 engages with the upper engagement portion 6d by means of elasticity of the operation spring 51, whereby the connector 5 is pressed to be locked. Subsequently, when the connector 5 is re-pressed via the operation member 5A, the engagement pin 5e is released from the lower engagement portion 6e by means of elastic restoring force of the elastic arm 6g of the lock member 6, to reach the second switch portion 6c (FIG. 37(b)). When pressing force applied to the operation member 5A is released, the engagement pin 5e moves to the lower engagement portion 6e through the guide groove 6a by means of elasticity of the operation spring 51, and thus the operation member 5A and the connector 5 return to the original position (FIG. 37(a)). The whole operation of the powder inhalator will be described later.

Figure 25:
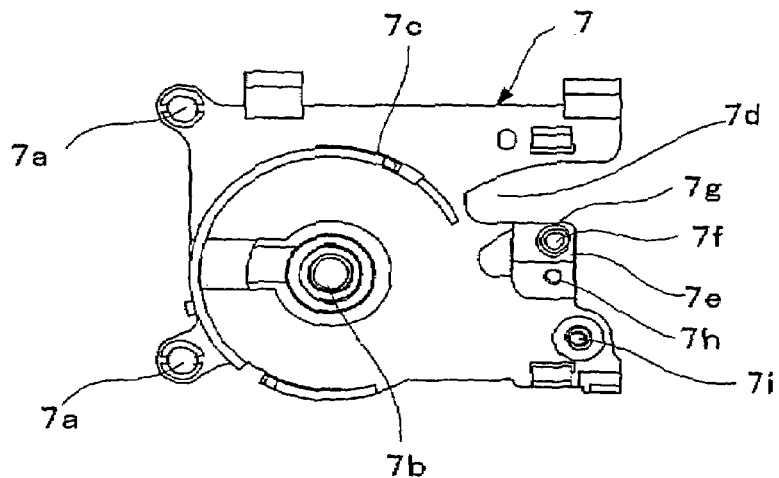
FIG. 25 is a plan view illustrating a base of the powder inhalator.
Figure 26:
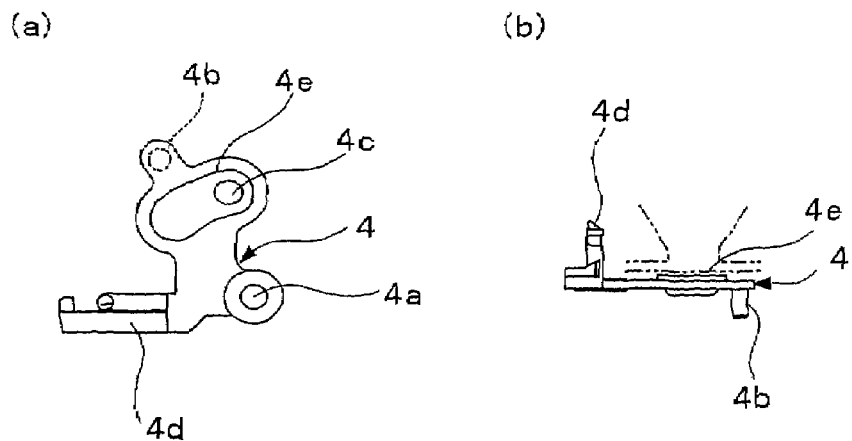
FIG. 26(*a*) is a plan view illustrating a drug carrier of the powder inhalator.
Figure 28:
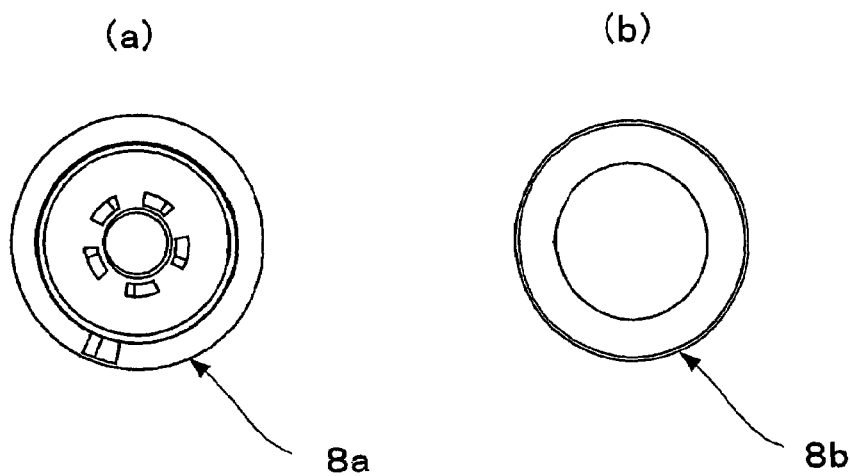
FIG. 28 is a plan view illustrating a counter of the powder inhalator.

The drug carrier 4 is provided with a shaft opening 4a at one end thereof, and a latch pin 4b at the other end thereof as shown in FIG. 25. A single-dose measuring recess 4c having a spherical concave shape and provided with a bottom is formed at a point midway between the shaft opening 4a and the latch pin 4b. The drug carrier 4 is further provided with a ratchet 4d which engages with the counter 8 for rotating the same. The measuring recess 4c may be a through hole.

The upper surface of the drug carrier 4 is partially raised to form an arc-shaped sliding portion 4e as view in a plan, at one end of which the measuring recess 4c is located. Thus, the sliding portion 4e alone of the drug carrier 4 contacts the bottom surface of the thick-wall part 3g at the surrounding portion of the drug discharge aperture 3b of the supply member 3 even when the measuring recess 4c moves in a circular manner.

The drug carrier 4 is slidably supported by the pivot pin 7i of the base 7 as described later. The drug carrier 4 engages with the connector 5 by inserting the latch pin 4b of the drug carrier 4 into the latching slot 5b.

The sliding portion 4e of the drug carrier 4 elastically contacts the bottom surface of the thick-wall part 3g at the surrounding portion of the drug discharge aperture 3b of the supply member 3 by elastically energizing the drug carrier 4 upwardly by means of a press member 9, which will be described later. Thus, the sliding portion 4e of the drug carrier 4 contacts tightly the surrounding portion of the drug discharge aperture 3b of the hopper 3a, which prevents leakage of the powdered drug from the measuring recess 4c of the drug carrier 4.

The base 7 is provided with an engagement aperture 7a and a counter support-shaft 7b as shown in FIG. 24, etc. A counter support-ring 7c is provided at the surrounding portion of the support-shaft 7b. A notch 7d is provided in a range in which the engagement pin 4b moves due to the sliding action of the drug carrier 4.

The base 7 is provided further with an attachment portion 7e for the press member 9. The attachment portion 7e is provided with a spring support-shaft 7g having an engagement aperture 7f and a fix pin 7h. The bottom surface of the press member 9 is provided with a boss 9c having an engagement projection 9a and an engagement aperture 9b. As shown in FIG. 27(b), the press member 9 is spring-forced upwardly by engaging the engagement aperture 9b of the press member 9 with the fix pin 7h of the base 7, and engaging the engagement projection 9a of the press member 9 with the spring support-shaft 7g of the base 7 through which the press spring (coil spring) 10 is inserted. A pivot pin 7i is formed in the vicinity of the attachment portion 7e of the press member 9.

A counter 8 having a known structure can be employed. More specifically, the counter 8 is provided with a disk with a cam 8a representing the ones digit and a wheel with a cam 8b representing the tens digit. The disk with cam 8a is rotatably supported by the counter support-shaft 7b of the base 7, and is fitted into the wheel with cam 8b, and is also supported by means of the counter support ring 7c.

The ratchet 4d is activated by the sliding action of the drug carrier 4 and causes the disk with cam 8a representing the ones digit rotates increasing the count. The wheel with cam 8b rotates increasing the count at the time of 10th dose. Thus, the dose number can be displayed the wheel with cam 8b attains full count.

It may be configured to leak static electricity by imparting conductivity to material of the supply member 3, the drug carrier 4 and the connector 5 by adding a conductive filler, such as carbon, thereto.

The members, to which conductivity is imparted, are not limited to the supply member 3, the drug carrier 4 and the connector 5.

Hereinafter, assembling processes of the powder inhalator will be described.

Initially, the lock member 6 is contained in the containing unit 1t of the lower-side housing 1b as shown in FIG. 31. Thereafter, the connector 5 is attached to the lower housing 1b to be located on the lock member 6. During this process, the guide shaft 1m of the lower-side housing 1b is inserted into the guiding slot 5c of the operation member 5. The spring-latch projection 1q of the lower-side housing 1b is inserted through the insertion slot 5d of the connector 5. One end of the operation spring 51 inserts through the spring attachment shaft 5f of the connector 5, and the other end thereof is latched at the spring-latch projection 1q of the lower-side housing 1b.

Figure 33:
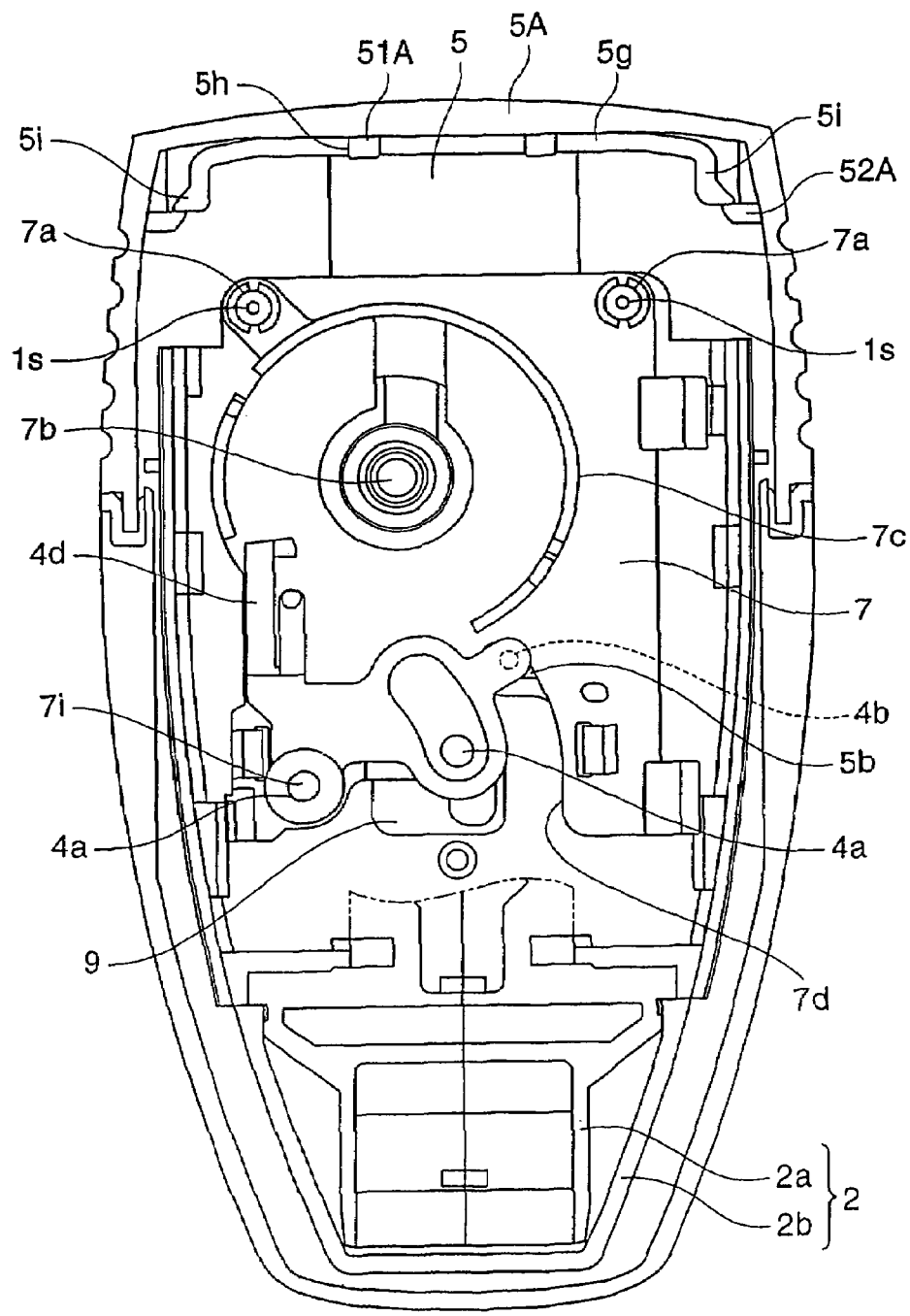
FIG. 33 is a plan view illustrating a stage of assembling the powder inhalator.

Subsequently, as shown in FIG. 33, the base 7 is mounted on the base receiver 1r of the lower-side housing 1b and the position of the base 7 is then determined by engaging the engagement aperture 7a of the base 7 with the engagement projection 1s of the lower-side housing 1b. Thereafter, the press member 9 is installed on the base 7 and the drug carrier 4 is then mounted on the base 7 and the press member 9 as described above. During this process, the aperture for pivoting 4a of the drug carrier 4 and the pivot pin 7i of the base 7 are engaged with each other, and the engagement pin 4b of the drug carrier 4 then inserts into the latching slot 5*b* of the connector 5, whereby the drug carrier 4 engages with the operation member 5.

The counter 8 is installed on the base 7, and the engagement groove 2*e* of the mouthpiece 2 then engages with the pinching projection 1*g* of the lower-side housing 1*b* as described above.

Subsequently, the position of the counter 8 is determined by a cover 3*e* of the supply member 3 by locating the supply member 3 on the drug carrier 4, and inserting the through hole 3*f* of the supply member 3 and the aperture for pivoting 4*a* of the drug carrier 4 through the pivot pin 7*i* of the base 7 in such a way that the drug carrier 4 is slidably supported as shown in FIG. 23.

The position of the supply member 3 is determined by means of the positioning unit formed inside of the upper-side housing 1*a* by joining the upper-side housing 1*a* to the lower-side housing 1*b*. And then, the pinching projection 1*g* of the upper-side housing 1*a* engages with the engagement groove 2*e* of the mouthpiece 2. Then, the cover 2*b* engages with the body 2*a* of the mouthpiece 2.

As shown in FIG. 33, the operation member 5A covers the rear portion of the housing body 1, and the engagement projection 1A engages with the engagement aperture 5*h* of the attachment portion 5*g* of the connector 5. The supply member 3 is not shown in FIG. 33.

The powder inhalator configured thus will be operated as described below.

The drug carrier 4 is positioned at a drug loading position where the measuring recess 4*c* of the drug carrier 4 aligns with the drug discharge aperture 3*b* of the supply member 3 when the protecting cap 1*c* is attached to the powder inhalator as shown in FIG. 23.

As shown in FIGS. 34 through 36, when the protecting cap 1*c* is removed and the operation member 5A is then pressed to lock the connector 5 with holding the housing 1A, the drug carrier 4 slides and thus the measuring recess 4*c* moves into gap in the vicinity of an air-intake groove 32 of the hopper 3*a* from the drug loading position as represented by a chain double-dashed line.

During this movement, the powdered drug loaded within the measuring recess 4*c* is scraped by the thick-wall part 3*g* at the surrounding portion of the pharmaceutical discharge aperture 3*b*. Thus, one dose of the powdered drug is carried to the gap at the vicinity of the air-intake groove 32.

Subsequently, the inside of the housing body 1 is rendered to be a negative pressure by means of air-intake pressure of a patient when the patient inhales air into the housing 1A from the air-intake aperture 2*f* of the mouthpiece 2. Thus, external air is inhaled into the housing body 1 from the air intake 1*i* of the housing body 1 to reach the drug inhalation channel 2*c* of the mouthpiece 2 through the air-intake groove 32 of the mouthpiece 2 shown by the arrow in FIG. 34. Thus, air impact is applied to the powdered drug loaded in the measuring recess 4*c* of the drug carrier 4, and the powdered drug is then dispersed within the drug inhalation channel 2*c* of the mouthpiece 2. Hence, the powdered drug reaches the inside of lungs with the inhaled air through the air-intake aperture 2*f*.

The operation member 5 is re-pressed to be returned to the original position with holding the hosing 1A, and thus the drug carrier 4 swings back to return to the drug loading position under the drug discharge 3*b* of the supply member 3.

As shown in FIG. 35(*b*), a window 1*j* through which the display of the counter 8 can be read out is covered by the operation member 5A when a user presses the operation member 5A, which prevents the user from seeing the display of the number of doses while the counter 8 is changing. Thus, the user only sees the display of the number of doses through the window 1*j* after the display has changed. Therefore, the user does not misunderstand the number of doses indicated by the counter display while it is changing.

As shown in FIG. 23, when the powder inhalator is not being used (when carrying it, etc.), the housing 1A is entirely enveloped because when the front portion of the housing 1A is covered with the protecting cap 1*c*, the rear end of the protecting cap 1*c* engages with the front end of the operation member 5A via a seal member 11*c*.

The powder inhalator is discarded when the powdered drug within the hopper 3*a* is completely exhausted.

The moisture-proofness of the powder inhalator can also be improved by configuring the inside of the powder inhalator in such a way as to insert a tablet-like drying agent.

The cap-shaped operation member 5A and the protecting cap 1*c* are preferably formed from a material with low moisture permeability, such as high-density polyethylene, polypropylene or the like, in view of the objective to be attained. Such materials may eliminate the necessity of employing the seal material 11*c*.

EMBODIMENT 3

Figure 38:
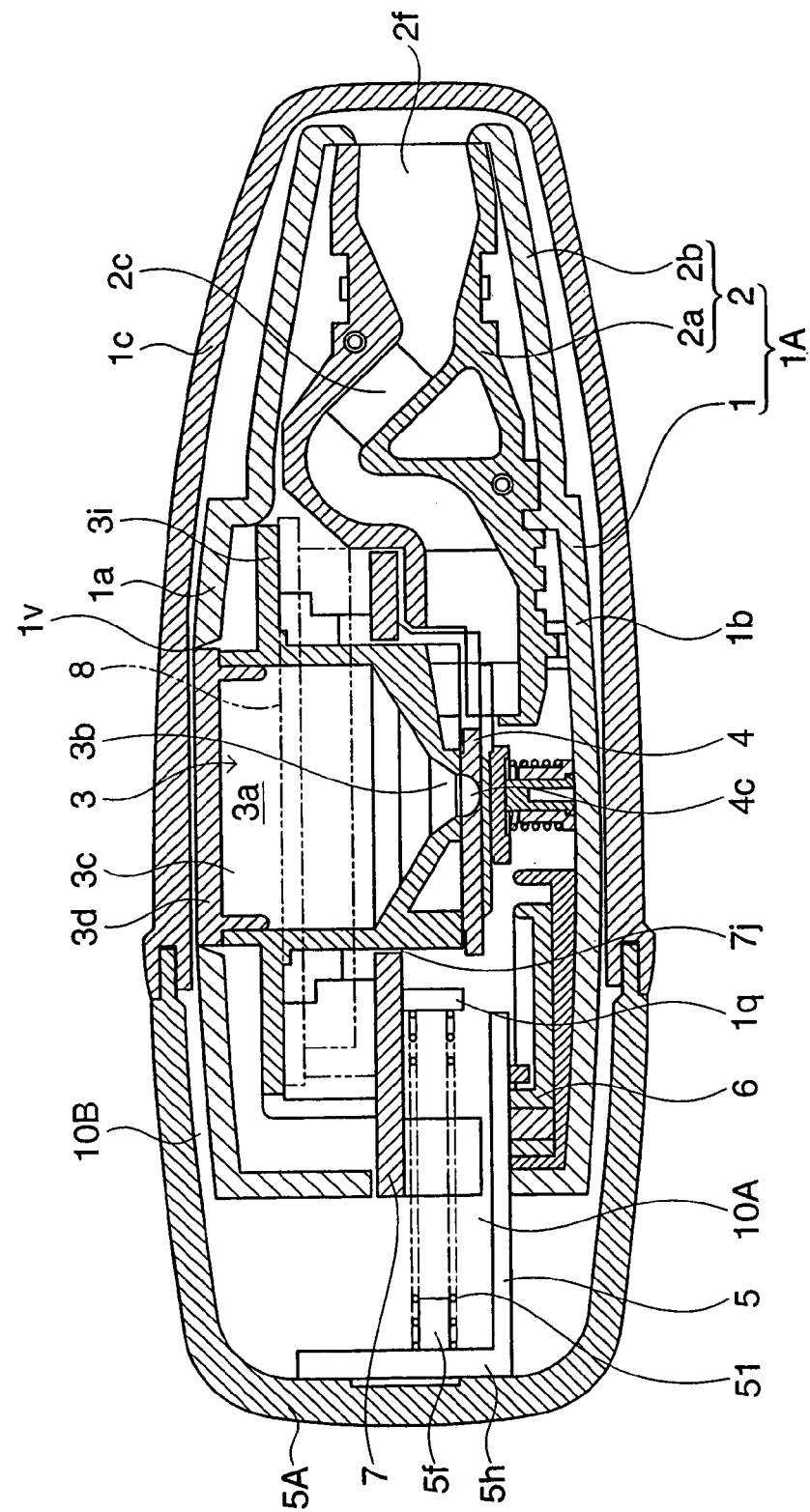
FIG. 38 is an elevational cross sectional view illustrating a powder inhalator according to Embodiment 3 of the present invention.
Figure 39:
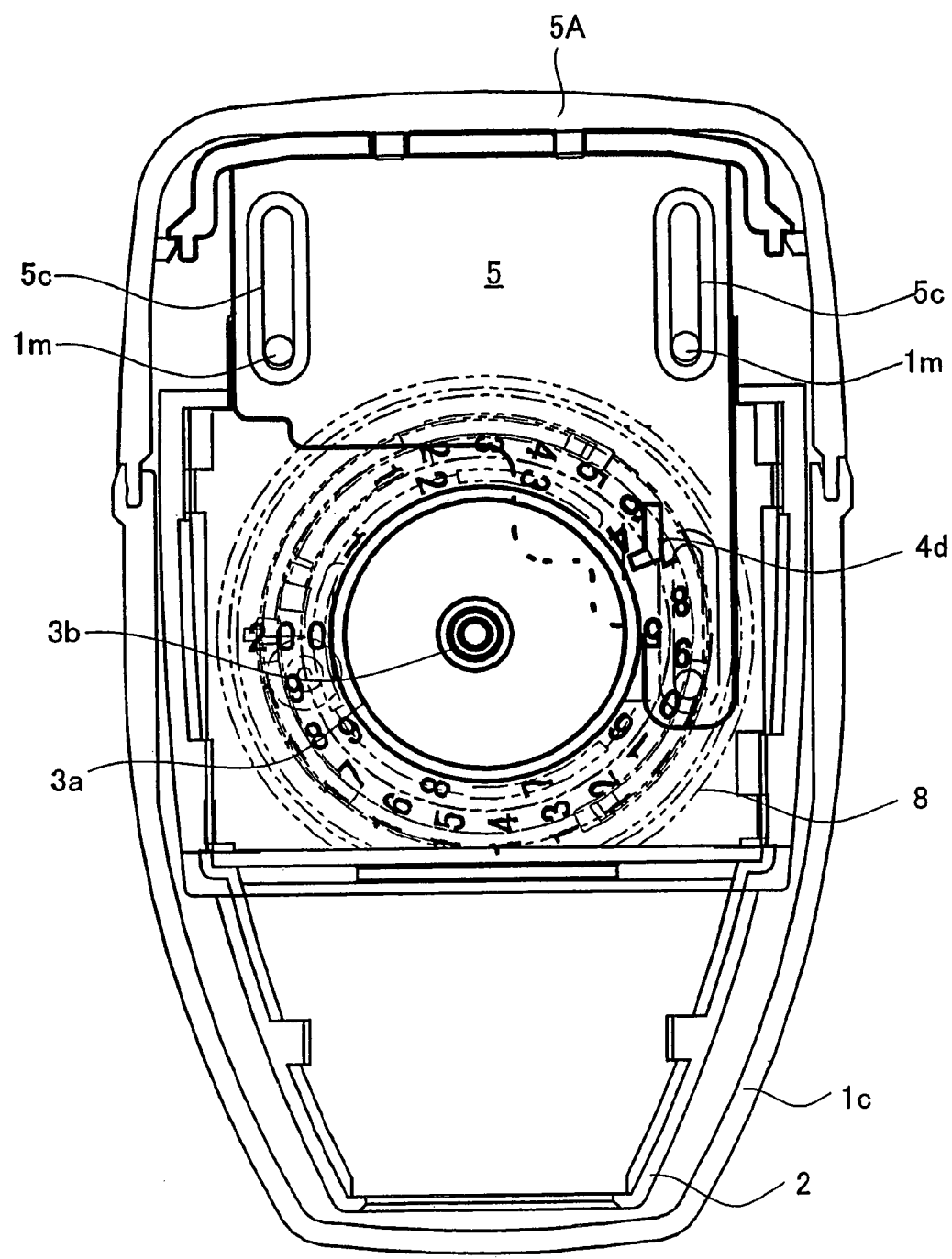
FIG. 39 is a plan view illustrating the position relation among a counter, a hopper and a connector of the powder inhalator.
Figure 40:
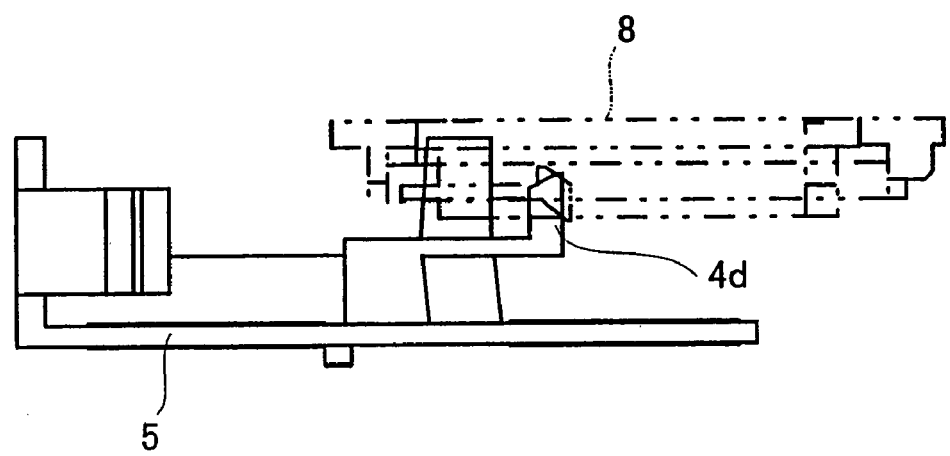
FIG. 40 is a side elevation view illustrating the position relation between a counter and a ratchet of the powder inhalator.
Figure 42:
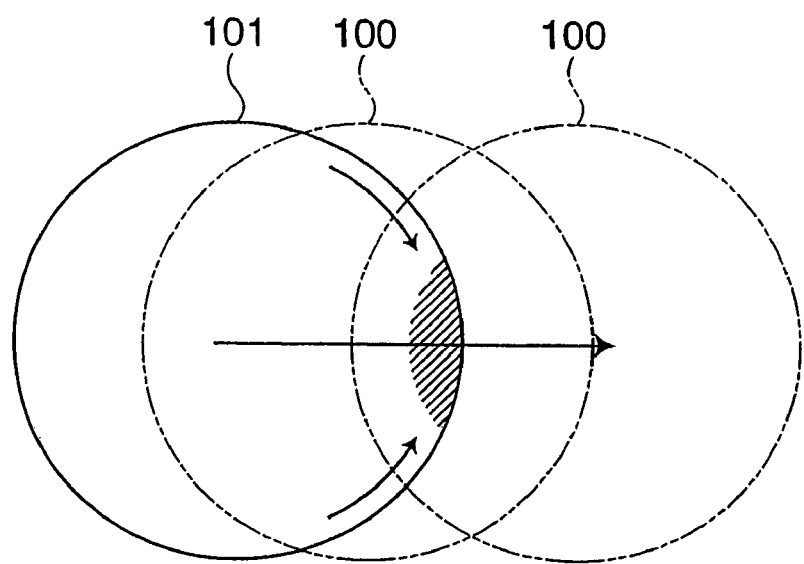
FIG. 42 is a view schematically illustrating a scraping operation of the powdered drug by the powder inhalator.

FIG. 38 is an elevational cross sectional view illustrating a powder inhalator. FIG. 39 is a plan view illustrating the position relation among a counter 8, a hopper 3*a* and a connector 5 of the powder inhalator. FIG. 40 is a side elevation view illustrating the position relation between a counter 8 and a ratchet 4 of the powder inhalator.

The basic configuration of the powder inhalator of the present embodiment is the same as that of the Embodiment 2. More specifically, the powder inhalator is provided with a housing 1A having a housing body 1 and a mouthpiece 2, a protecting cap 1*c*, a supply member 3 for containing powdered drug for a large number of doses, a drug carrier 4 for carrying a dose of the powdered drug, an operation member 5A for operating the drug carrier 4, a connector 5 for establishing connection between the drug carrier 4 and the operation member 5A, a lock member 6 for locking the operation member 5A via the connector 5, a base 7 and a counter 8 for displaying the number of doses.

The powder inhalator of the present embodiment is different from that of the Embodiment 2 in that the ring-shaped counter 8 is located around the hopper 3*a* so that the dose numbers are counted by rotating the counter 8 around the hopper 3. As described above, a space around the hopper 3*a* is utilized to contain the counter 8 and thus a length of the powder inhalator is shortened to enhance the portability thereof. An opening 1*v* for opening/closing a lid 3*d* is provided at a location corresponding to the lid 3*d* of the hopper 3*a* of the housing 1A. Thus, the lid 3*d* can be opened/closed requiring no disassembling the housing 1A, which is also different from the powder inhalator of other embodiments. In the present embodiment, the same or similar parts are designated by the same numerals as in the Embodiment 2, and thus the detailed descriptions are omitted.

The present embodiment adopts the following configuration so that the counter 8 is located around the hopper 3*a*.

As shown in FIG. 38, the base 7 is provided with a large diameter aperture 7*j*, into which the hopper 3*a* is fitted. The counter 8 placed on the base 7 is located around the hopper 3*a*. An external rib 3*i* is provided at the hopper 3*a* to determine the position of the counter 8. Accordingly, the base 7 needs not to be provided with neither the cover 3e for determining the position of the counter 8 nor the counter support-shaft 7b.

The powder inhalator is assembled as follows. The counter 8 is placed on the base 7. In this state, the counter 8 is located around the large diameter aperture 7j of the base 7. Subsequently, the hopper 3a is fitted into the large diameter aperture 7j of the base 7 and the counter 8 is then pressed from above with the external rib 3i of the hopper 3a.

As shown in FIG. 40, the ratchet 4d for rotating the counter 8 is formed at the connector 5. The ratchet 4d is reciprocated in a straight line with the operation of the operation member 5A so as to rotate the counter 8. The window 1j is provided at a location corresponding to the attachment location for the counter 8, through which the counter 8 can be read out. Air intakes 1i are provided at both sides of the front portion of the upper housing 1a. The spring-latch projection 1q is provided at the base 7.

The powder inhalator of the present invention is configured as described above, thus enabling the various effects described below to be obtained.

According to the powder inhalator of the present invention, the drug carrier is slidably disposed so that the measuring recess moves in a circular manner by sliding the drug carrier. Thus, when the measuring recess moves toward the drug inhalation channel, the powdered drug flows along the aperture wall of the drug discharge aperture, whereby the powdered drug can be scraped smoothly. Thus, the powdered drug is prevented from becoming clogged between the supply member and the drug carrier. Therefore, it is possible to prevent any lowering of the ability to measure the powdered drug and to avoid deterioration in the operability of the drug carrier. Moreover, production cost can be reduced by simplifying the mechanism in which the measuring recess moves between the drug discharge aperture of the supply member and the air-intake channel.

The stroke of the measuring recess can be made shorter than the stroke of the operation member of the drug carrier by positioning the measuring recess between the center of the pivotal movement of the drug carrier and the point at which the operation member engages the drug carrier. Therefore, the amount of static electricity that is accumulated can be reduced, which prevents the quantitative accuracy and particle-containing ratio from being lowered.

When the operation member is configured with a push-button and the measuring recess is designed to move from the drug loading position to the drug dispersion position by pressing the operation member, the operation member does not need to move the distance that is required to remove the protecting cap from the inhalation opening in the conventional powder inhalator in which the operation member also serves as the protecting cap. Thus, the operating distance of the operation member can be shortened, which reduces the resulting amount of static electricity.

Static electricity produced by friction can be leaked when conductivity is imparted to the supply member, the drug carrier and the operation member, thereby allowing extremely small amounts of powdered drug to be consistently measured and a high particle-containing ratio to be attained.

In the above-described mechanism in which the measuring recess moves between the drug discharge aperture of the supply member and the air-intake channel, the measuring recess having a spherical concave shape and provided with a bottom can prevent the powdered drug from being reloaded even when a patient erroneously pushes the operation member two or more times without inhaling the pharmaceutical drug. Thus, the present invention can prevent more than one dose of the drug from being inhaled into the lungs of the patient, and can ensure that the one dose of drug will be taken into the lungs rather than being left remaining in the powder inhalator.

A high moisture-proofing effect can also be obtained by employing the components that constitute the powder inhalator (operation member) as a moisture-proof case. This is possible because the powder inhalator of the present invention is configured as follows: an aperture portion for operation is provided at the rear side of the housing, the operation member is formed like a cap, the operation member is designed to move back and forth to cover the rear portion of the housing, a connector inserted into the aperture is used to connect the operation member to the drug carrier in such a way that the rear end of the protecting cap and the front end of the operation member join together to envelope the whole housing when the protecting cap is pressed onto the housing. As a result, it is not necessary to insert the powder inhalator into, or remove it from, a moisture-proof case, which improves its portability.

Also, the external air inflow path that extends into the housing is lengthened because there is a gap formed between the operation member and the housing. Therefore it is difficult for external air to flow into the housing even when the protecting cap is removed from the housing, which prevents a lowering of the moisture-proof effect.

When the protecting cap is attached to the housing, the operation member cannot be pressed while holding the housing. Thus, the operation member is locked by the protecting cap, which can prevent erroneous operation.

Moreover, the moisture-proof effect can be further improved under use when a baffle for preventing air from flowing into the gap is formed between the housing and the operation member.

The moisture-proof effect can be even further improved during non-use if a seal member is attached to at least one of the rear end of the operation member or the front end of the protecting cap, and the protecting cap is joined to the operation member via the seal member.

The invention claimed is:

1. A powder inhalator comprising:
   a housing;
   a supply member for holding a powdered drug for a large number of doses and having a drug discharge aperture at its bottom surface;
   a drug carrier having a flat upper surface, to which the powdered drug is supplied from the drug discharge aperture of the supply member, and having on its flat upper surface measuring recess that has a volume equivalent to one dose of the drug; and
   an operation member disposed so as to move freely back and forth, and operate the drug carrier,
   the drug carrier moving in contact with the bottom surface of the supply member to carry the powdered drug loaded into the measuring recess from the position of the drug discharge aperture to an air inhalation channel,
   wherein the drug carrier is supported pivotably in the housing so that the measuring recess reciprocates in a circular manner, relative to the drug discharge aperture of the supply member, by pivoting the drug carrier;
   wherein the flat surface is raised to form an arc-shaped sliding portion, and at one end of the flat surface the measuring recess is positioned, thereby the sliding portion alone of the drug carrier contacts the bottom surface of a surrounding portion of the drug discharge aperture of the supply member when the measuring recess moves in the circular manner.

2. The powder inhalator according to claim 1 wherein the measuring recess is located at a position between the center of the pivotal movement of the drug carrier and the point at which the operation member engages the drug carrier.

3. The powder inhalator according to claim 2, wherein the operation member is a pushbutton and the operation member is pressed to move the measuring recess into the air inhalation channel.

4. The powder inhalator according to claim 3, wherein electrical conductivity is imparted to the supply member, the drug carrier and the operation member by adding a conductive filler, so as to leak static electricity.

5. The powder inhalator according to claim 4, wherein the measuring recess is a spherical concave shape and provided with a bottom.

6. The powder inhalator according to claim 3, wherein the measuring recess is a spherical concave shape and provided with a bottom.

7. The powder inhalator according to claim 2, wherein electrical conductivity is imparted to the supply member, the drug carrier and the operation member by adding a conductive filler, so as to leak static electricity.

8. The powder inhalator according to claim 7, wherein the measuring recess is a spherical concave shape and provided with a bottom.

9. The powder inhalator according to claim 2, wherein the measuring recess is a spherical concave shape and provided with a bottom.

10. The powder inhalator according to claim 1 wherein the operation member is a pushbutton and the operation member is pressed to move the measuring recess into the air inhalation channel.

11. The powder inhalator according to claim 10, wherein electrical conductivity is imparted to the supply member, the drug carrier and the operation member by adding a conductive filler, so as to leak static electricity.

12. The powder inhalator according to claim 11, wherein the measuring recess is a spherical concave shape and provided with a bottom.

13. The powder inhalator according to claim 10, wherein the measuring recess is a spherical concave shape and provided with a bottom.

14. The powder inhalator according to claim 1, wherein electrical conductivity is imparted to the supply member, the drug carrier and the operation member by adding a conductive filler, so as to leak static electricity.

15. The powder inhalator according to claim 14, wherein the measuring recess is a spherical concave shape and provided with a bottom.

16. The powder inhalator according to claim 1, wherein the measuring recess is a spherical concave shape and provided with a bottom.

* * * * *